US009693742B2

(12) United States Patent
Grasruck et al.

(10) Patent No.: US 9,693,742 B2
(45) Date of Patent: Jul. 4, 2017

(54) METHOD FOR GENERATING A CONTRAST MEDIUM-ASSISTED X-RAY IMAGE AND X-RAY SYSTEM

(75) Inventors: Michael Grasruck, Nürnberg (DE); Gregor Jost, Berlin (DE)

(73) Assignees: SIEMENS AKTIENGESELLSCHAFT, Munich (DE); BAYER INTELLECTUAL PROPERTY GMBH, Nordrhein-Westfalen (DE)

( * ) Notice: Subject to any disclaimer, the term of this patent is extended or adjusted under 35 U.S.C. 154(b) by 327 days.

(21) Appl. No.: 13/979,154

(22) PCT Filed: Jan. 17, 2012

(86) PCT No.: PCT/DE2012/000041
§ 371 (c)(1),
(2), (4) Date: Sep. 3, 2013

(87) PCT Pub. No.: WO2012/097801
PCT Pub. Date: Jul. 26, 2012

(65) Prior Publication Data
US 2014/0005533 A1    Jan. 2, 2014

(30) Foreign Application Priority Data
Jan. 18, 2011   (DE) ................. 10 2011 009 147

(51) Int. Cl.
*A61B 6/03*    (2006.01)
*A61B 6/00*    (2006.01)
(Continued)

(52) U.S. Cl.
CPC ............ *A61B 6/4042* (2013.01); *A61B 6/032* (2013.01); *A61B 6/06* (2013.01); *A61B 6/4035* (2013.01);
(Continued)

(58) Field of Classification Search
CPC ............. A61B 6/00; A61B 6/03; G01N 23/04
See application file for complete search history.

(56) References Cited

U.S. PATENT DOCUMENTS 3,854,049 A    12/1974  Kelcz
4,478,816 A    10/1984  Ledley et al.
(Continued)

FOREIGN PATENT DOCUMENTS

CN        101484073 A      7/2009
WO       WO 9703993 A1    2/1997
(Continued)

OTHER PUBLICATIONS

International Search Report PCT/ISA/210 for PCT/DE2012/000041 dated Jul. 11, 2012.
(Continued)

*Primary Examiner* — Tse Chen
*Assistant Examiner* — Nate S Sunwoo
(74) *Attorney, Agent, or Firm* — Harness, Dickey & Pierce, PLC

(57) ABSTRACT

A method is disclosed for generating at least one x-ray image of a patient having incorporated contrast medium, using x-rays having an energy spectrum and an x-ray detector. The energy spectrum is modified by at least one first filter arranged in the beam path in front of the patient, the patient absorbing a dose in order to generate detector data for the x-ray image and the x-ray image having a CNR value which represents the ratio of the maximum contrast in the image to the noise. The energy spectrum and contrast medium are matched to each other, taking into account the thickness of the patient to be x-rayed, in such a way that an optimization criterion which is taken from an x-ray image that is generated or simulated by way of trials is maximized. Furthermore, an x-ray system is also disclosed.

31 Claims, 10 Drawing Sheets

(51) Int. Cl.
*A61B 6/06* (2006.01)
*A61K 49/04* (2006.01)
*G21K 1/10* (2006.01)

(52) U.S. Cl.
CPC ............ *A61B 6/4441* (2013.01); *A61B 6/481* (2013.01); *A61B 6/501* (2013.01); *A61B 6/504* (2013.01); *A61B 6/544* (2013.01); *A61B 6/583* (2013.01); *A61K 49/04* (2013.01); *A61K 49/0438* (2013.01); *G21K 1/10* (2013.01)

(56) References Cited

U.S. PATENT DOCUMENTS

| | | | |
|---|---|---|---|
| 5,195,115 A * | 3/1993 | Schiller | G01N 23/207 378/158 |
| 6,060,712 A * | 5/2000 | Morgan | G01T 1/1615 250/363.04 |
| 7,583,779 B2 | 9/2009 | Tkaczyk et al. | |
| 2005/0082491 A1 * | 4/2005 | Seppi | H01L 27/14676 250/370.11 |
| 2007/0114424 A1 | 5/2007 | Danielsson et al. | |
| 2007/0242797 A1 * | 10/2007 | Stewart | A61B 6/02 378/16 |
| 2008/0310582 A1 * | 12/2008 | Flohr | A61K 49/04 378/5 |
| 2009/0086882 A1 * | 4/2009 | Grasruck | A61B 6/507 378/4 |
| 2010/0002828 A1 | 1/2010 | Miura | |
| 2010/0204622 A1 * | 8/2010 | Hwang | A61B 5/6831 601/41 |
| 2010/0278749 A1 * | 11/2010 | Bonitatibus, Jr. | A61K 49/0428 424/9.32 |

FOREIGN PATENT DOCUMENTS

| | | |
|---|---|---|
| WO | WO 9703994 A1 | 2/1997 |
| WO | WO-2007/051739 A2 | 5/2007 |
| WO | WO-2007/058600 A1 | 5/2007 |
| WO | WO 2007051739 A2 | 5/2007 |
| WO | WO 2007058600 A1 | 5/2007 |

OTHER PUBLICATIONS

Written Opinion PCT/ISA/237 for PCT/DE2012/000041 dated Jul. 11, 2012.
Chinese Office Action issued in Chinese Patent Application No. 2012800056148, dated Jan. 5, 2015.
Korean Office Action issued in Korean Patent Application No. 10-2013-7021165, dated Feb. 16, 2015.
Pietsch et al.: "Efficacy and safety of lanthanoids as X-ray contrast agents", in. Eur J Radio!, Epub ahead of print 2009; 2009.
Kalender et al.: "Application- and patient size-dependent optimization of x-ray spectra for CT", Medical Physics (2009), vol. 36, No. 3, p. 993-1007. (53 refs.), CODEN: MPHYA6 ISSN 0094-2405, Journal paper (English); 2009.

* cited by examiner

METHOD FOR GENERATING A CONTRAST MEDIUM-ASSISTED X-RAY IMAGE AND X-RAY SYSTEM

PRIORITY STATEMENT

This application is the national phase under 35 U.S.C. §371 of PCT International Application No. PCT/DE2012/000041 which has an International filing date of Jan. 17, 2012, which designated the United States of America and which claims priority to German patent application number DE 10 2011 009147.5 filed Jan. 18, 2011, the entire contents of each of which are hereby incorporated herein by reference.

FIELD

At least one embodiment of the invention generally relates to a method for generating at least one X-ray image of a patient with incorporated contrast medium, using X-ray radiation generated at an anode and having an energy spectrum of bremsstrahlung and characteristic radiation, and/or an X-ray detector, wherein the energy spectrum used is modified by at least one filter arranged in the beam path in front of the patient, the patient absorbs a dose in order to generate detector data for the X-ray image and the X-ray image has a CNR value which represents the ratio of the maximum contrast between soft tissue and contrast medium in the image to the noise. At least one embodiment of the invention also generally relates to an X-ray system for generating at least one X-ray image of a patient with incorporated contrast medium.

BACKGROUND

The non-invasive imaging of internal body structures and organs by way of computed tomography (CT) is a widely used method in medical diagnostics. A high level of contrast can be achieved between bones and soft tissue parts. However, the contrast between the different soft tissue parts is suitable for diagnostic purposes to only a limited extent, as a result of small absorption differences.

Therefore, in order to increase the contrast between particular body structures and/or body fluids, contrast media are utilized. These contrast media contain an element which strongly absorbs X-ray radiation, in order to achieve an enhanced image contrast in relation to the surrounding tissues which have low absorption. Today, in radiological imaging using X-ray radiation, iodine-containing contrast media are used to image body fluids, organs and pathological processes. However, the absorption properties of iodine do not make the element the optimum material for contrast enhancement in X-ray diagnostics using tube voltages of >80 kV. This applies, in particular, to computed tomography, in which today tube voltages of up to 140 kV are used.

In the energy range of the X-ray radiation used, the X-ray density of contrast media increases in proportion to the atomic number of the contrast-creating element. The use of contrast media having higher atomic numbers as absorptive elements is therefore of particular interest for CT and, in addition to lanthanides (Pietsch et al., "Efficacy and safety of lanthanoids as X-ray contrast agents" in Eur J Radiol, Epub ahead of print 2009; WO 2007/051739), hafnium, rhenium, tantalum and tungsten have also been proposed (WO 97/03994; WO 97/03993). What all contrast media have in common, however, is that, despite the good safety properties such media possess, undesirable side effects can occur.

Nevertheless, the majority of contrast media currently used for X-ray diagnostics are based on iodine as the main X-ray attenuating component. Current equipment technology is optimized for this. In selecting elements for contrast media, the general rule is that the element should have the highest possible atomic number, since the X-ray absorption rises strongly with increasing atomic number. As the atomic number increases, the K-edge of the element used becomes displaced into the diagnostic energy window for X-ray radiation. At energies above the K-edge, the absorption increases suddenly, so that the design of X-ray devices is no longer based on the principle that the softest possible X-ray radiation gives the best contrast between water and the contrast medium.

SUMMARY

At least one embodiment of the invention is directed to reducing the applied radiation dose $D\gamma$ during recording of an X-ray image, while obtaining imaging which is improved or at least not worsened as compared with the prior art. Furthermore, given the existing incorporation of contrast medium in the region to be imaged, the contrast medium dose, that is, the contrast medium concentration in the body, should be reduced as far as possible.

Advantageous developments of the invention are the subject matter of the subclaims.

A method for generating at least one X-ray image of a patient with incorporated contrast medium, using X-ray radiation generated at an anode and having an energy spectrum of bremsstrahlung and characteristic radiation, and an X-ray detector, wherein the energy spectrum used is modified by at least one first filter arranged in the beam path in front of the patient, the patient absorbs a dose in order to generate detector data for the X-ray image and the X-ray image has a CNR value which represents the ratio of the maximum contrast in the object under investigation to the noise, wherein, according to the invention, taking account of the thickness of the patient to be X-rayed, the energy spectrum and the contrast medium are adjusted to one another by an additional filter such that an optimization criterion taken from an experimentally generated or simulated X-ray image, is maximized.

What is proposed in one embodiment, in particular, therefore is an X-ray system for the diagnostic tomographic representation of an object, for example, a patient, having at least one X-ray tube-detector unit for determining the attenuation of the X-ray radiation by the object. From this, tomographic images can be reconstructed with computer-assistance. This system comprises at least one special additional filter in front of at least one X-ray tube which spectrally modifies the emitted X-ray radiation such that an increase in the image contrast (quantifiable by the contrast-to-noise ratio) is brought about for contrast medium-accumulating tissue. The increase in the image contrast, aside from improving the image quality, can also be used for reducing the radiation dose or the contrast medium dose.

In addition to the aforementioned methods, the inventors also propose a method of an embodiment for recording X-ray images in the combination of an X-ray system with contrast media, wherein the contrast medium contains the elements rhenium, hafnium, tantalum or tungsten, wherein the contrast-to-noise ratio between the contrast medium-accumulating tissues and the surrounding tissue is increased and at least one additional filter with at least one element with the atomic numbers 77 (iridium), 78 (platinum), 79 (gold), 80 (mercury), 82 (lead) or 83 (bismuth) is introduced in front of the X-ray tube into the beam path and the radiation emitted by the X-ray tube is thereby modified spectrally.

The inventors also propose, in at least one embodiment, a method for recording X-ray images in combination with an X-ray system with contrast media, wherein the contrast medium contains at least one of the elements rhenium, hafnium, tantalum or tungsten, and at least one additional filter is provided in which at least one of the elements with the atomic numbers 77 (iridium), 78 (platinum), 79 (gold), 80 (mercury), 82 (lead) or 83 (bismuth) is used, and the at least one additional filter is introduced into the beam path between the X-ray tube and the patient in order to modify the radiation emitted by the X-ray tube spectrally, wherein computer-assisted tomographic images are reconstructed and the increase in the image contrast is used, alongside the rise in image quality, to reduce the radiation dose or the contrast medium dose.

The two latter methods can be used, in particular, in conjunction with CT angiography, dynamic contrast medium-assisted CT or a contrast medium-assisted CT tumor diagnostic technique.

In addition to an embodiment of the inventive method, an X-ray system for generating at least one X-ray image of a patient with incorporated contrast medium is proposed, comprising:

at least one anode for generating X-ray radiation with an energy spectrum of bremsstrahlung and characteristic radiation, at least one X-ray detector for pixel-wise measurement of the X-ray radiation penetrating the patient, at least one filter arranged in the beam path between the at least one anode and the at least one X-ray detector, which is placed in front of the patient and which modifies the energy spectrum used, wherein the patient absorbs a dose in order to generate detector data for the X-ray image and the X-ray image has a CNR value which represents the ratio of the maximum contrast between tissue enhanced by contrast medium and the surrounding tissues in the image, to the noise, at least one computer processor having at least one memory store in which computer programs with calculation and control instructions for execution are stored which control the X-ray system during operation and generate X-ray images from the received detector data, wherein, according to the invention at least one computer program is stored which carries out the method steps of one of the above methods during operation.

The X-ray system may be, for example, a C-arm system, a computed tomography system or a system for generating exclusively projectional X-ray images.

An embodiment of the invention also relates to the use of one of the X-ray systems described above:

in CT angiography for reducing the radiation dose received by the patient;

in CT angiography for increasing the image quality and thus the diagnostic validity, particularly in coronary angiography and in angiography for small and peripheral vessels;

in dynamic contrast medium-assisted CT imaging, for example, multi-phase liver diagnostics, brain perfusion, tumor perfusion or myocardial perfusion for reducing the radiation dose received by the patient;

in dynamic contrast medium-assisted CT imaging, for example, multi-phase liver diagnostics, brain perfusion, tumor perfusion or myocardial perfusion, for increasing image quality and thus the accuracy of the functional parameters derived therefrom;

in contrast medium-assisted CT tumor diagnostics for reducing the radiation dose received by the patient;

in contrast medium-assisted CT tumor diagnostics for increasing image quality and thereby the diagnostic validity;

in contrast medium-assisted CT imaging for reducing the contrast medium dose, in particular for renal insufficiency patients or patients with contrast medium intolerance;

in a dual energy CT examination of a patient, wherein the patient has one or more contrast media with different atomic numbers simultaneously or sequentially.

BRIEF DESCRIPTION OF THE DRAWINGS

The invention will now be described in greater detail making reference to the drawings, in which only the features necessary to an understanding of the invention are shown. The following reference signs and variables are used: 1: additional filter; 2: focus; 3: shaping filter; 4: collimators; 5: detector; 6: control and computer system; 7: radiation beam; C1: CT system; C2: X-ray tube; C3: detector; C4: X-ray tube; C4.1: additional filter; C5: detector; C6: gantry housing; C7: C-arm; C8: patient support; C9: system axis; C10: control and computer system; C11: contrast medium applicator; CNR: contrast-to-noise ratio $D\gamma$: radiation dose; $D\gamma(norm)$: normalizing factor for radiation dose; DK: contrast medium dose; DK(norm): normalizing factor for contrast medium dose; P: patient; Prg1-Prgn: computer programs; U: acceleration voltage.

In the drawings.

DETAILED DESCRIPTION OF THE EXAMPLE EMBODIMENTS

The inventors have identified the following:

The quality of the imaging or the delineation of two different tissue types or of a contrast medium-containing tissue from the surrounding contrast medium-free tissue can be defined quantitatively through the contrast-to-noise ratio (CNR) between the two tissue types or between tissues with and without contrast medium. This ratio is found from the image signal S1 and the image noise R1 of one tissue type or the contrast medium-containing tissue and from the signal S2 and the corresponding noise R2 of the other tissue type or of the contrast medium-free tissue. The ratio is determined using the following equation:

$$CNR = \frac{S_1 - S_2}{\sqrt{R_1^2 + R_2^2}}$$

The radiation dose given to the patient in radiological diagnosis is to be as low as possible in order not to expose the patient to ionizing radiation unnecessarily. Furthermore, as little contrast medium as possible should be present in the body in order to minimize potentially undesirable side effects. The aim of contrast medium-assisted X-ray diagnosis is the highest possible CNR at the lowest possible radiation dose. The radiation dose applied determines the image noise. Theoretically, the following relation between radiation dose $D\gamma$ and image noise R1 or R2 applies:

$$R \propto \frac{1}{\sqrt{D_\gamma}}.$$

I.e. on reduction of the radiation dose, the noise of the images increases, leading finally to a reduction in the CNR. An increase in the image signal S1, for example, by raising the contrast medium absorption based on filtration of the X-ray radiation leads to an increase in the CNR. Given a constant image quality, and therefore a constant CNR, the radiation dose can therefore be reduced. The combination of specifically filtered X-ray radiation and contrast media having high atomic numbers leads to an increase in the contrast medium signal and to a reduction in image noise. The resulting rise in the CNR can be used to reduce the radiation dose during the diagnostic imaging. This principle is demonstrated in example 2 described below.

Figure 1:
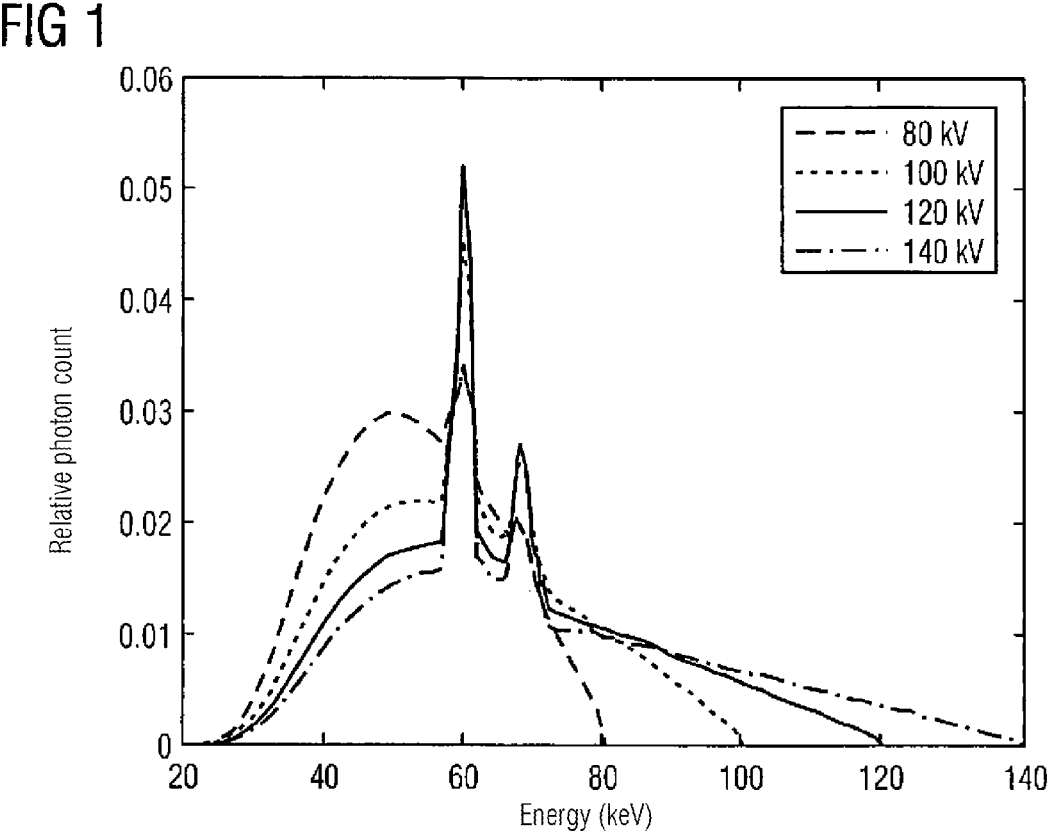
FIG. 1 shows photon spectra from a CT tube as a function of tube voltage.

The X-ray radiation used in radiological diagnosis is polychromatic, i.e. the wavelengths and thus the energies of the photons produced by an X-ray tube are not identical. The energy spectrum or photon spectrum of the X-ray radiation emitted by an anode is determined by the anode material and the X-ray tube voltage used (FIG. 1). In the field of CT diagnostics, it is almost exclusively tungsten anodes that are used nowadays.

Within the irradiated object, the emitted photon spectrum changes constantly because the absorption of X-ray radiation is energy-dependent and overlaying with scattered photons takes place. These associations are complex and cannot be described with simple mathematical relations. Thus, the photon spectrum changes, for example, depending on the irradiated volume, the penetration depth and the tissue composition.

The X-ray density of a contrast medium and therefore the image signal is determined by the attenuation coefficient of the contrast-creating element and the local concentration thereof in combination with the photon spectrum at the location of the physical interaction. The actual thickness of a patient's body must therefore also be taken into account.

Due to the high probability of interaction between the low energy photons and the tissue, the low-energy portions in the photon spectrum (in the region <50 keV) lead to a dose input but contribute to a small portion of the image generation. The use of photon energies at >50 keV leads, at the same radiation dose, to a reduction in the image noise R1 or R2. Monte-Carlo based simulations show that, in order to achieve a high soft-tissue contrast in the CT, given a minimum dose, photon energies in the range of 70 keV to 140 keV must be used (Kalender et al., Application and patient size dependent optimization of X-ray spectra for CT, Med. Phys. 36(3) 2009).

As distinct from this is the contrast medium-assisted CT, where photon energies in the range of 35 keV to 70 keV supply the highest CNR-to-dose ratio (Kalender et al., Application and patient size dependent optimization of X-ray spectra for CT, Med. Phys. 36(3) 2009). This distinction between non-contrast medium-assisted and contrast medium-assisted CT recordings is attributable to the spectral absorption characteristics of iodine (K-edge at 33 keV). The high absorption level of iodine in the range from 33 keV to approximately 70 keV outweighs the unfavorable dosage effect of low-energy photons. In the case of contrast media having elements of high atomic numbers and therefore also higher K-edge energies, for example, the lanthanides, Hf, Ta, Re or W, the optimum energy region of the contrast medium-assisted CT is shifted to higher energies in the range of 60 keV to 140 keV and is therefore almost identical to the optimum energy range for soft tissue contrast.

A concept of an embodiment of the invention lies therein that adjustment and delimiting of the energy spectrum used is carried out such that the energy spectrum lies as far as possible exclusively in the optimum region for contrast rendering, taking account of the thickness of the patient to be X-rayed and the contrast medium by adjusting the filter material, the filter thickness, the acceleration voltage, that is, the maximum energy of the braking spectrum, and the anode material. For this purpose, this energy spectrum is adjusted and delimited such that the greatest possible effectiveness is achieved with regard to CNR and dose.

What is proposed in one embodiment, in particular, therefore is an X-ray system for the diagnostic tomographic representation of an object, for example, a patient, having at least one X-ray tube-detector unit for determining the attenuation of the X-ray radiation by the object. From this, tomographic images can be reconstructed with computer-assistance. This system comprises at least one special additional filter in front of at least one X-ray tube which spectrally modifies the emitted X-ray radiation such that an increase in the image contrast (quantifiable by the contrast-to-noise ratio) is brought about for contrast medium-accumulating tissue. The increase in the image contrast, aside from improving the image quality, can also be used for reducing the radiation dose or the contrast medium dose.

By using the aforementioned additional filters, which can be inserted into the beam path, the photon spectrum emitted by the X-ray tube can be modified. In this way, the spectrum can be adapted to the contrast medium-assisted imaging. The additional filter consists of at least one element having an atomic number Z of greater than 22 (titanium). In particular, elements having higher atomic numbers of between Z=77 (iridium) and Z=83 (bismuth) are suitable. The additional filters can comprise one or more metals or an alloy, in particular made as a thin sheet or as enclosed mercury. The X-ray system, which comprises a plurality of additional filters having different materials and thicknesses can bring the filters, by way of a control unit, into the beam path automatically, depending on the application and use, in order to achieve the optimum energy distribution in the photon spectrum.

Figure 2:
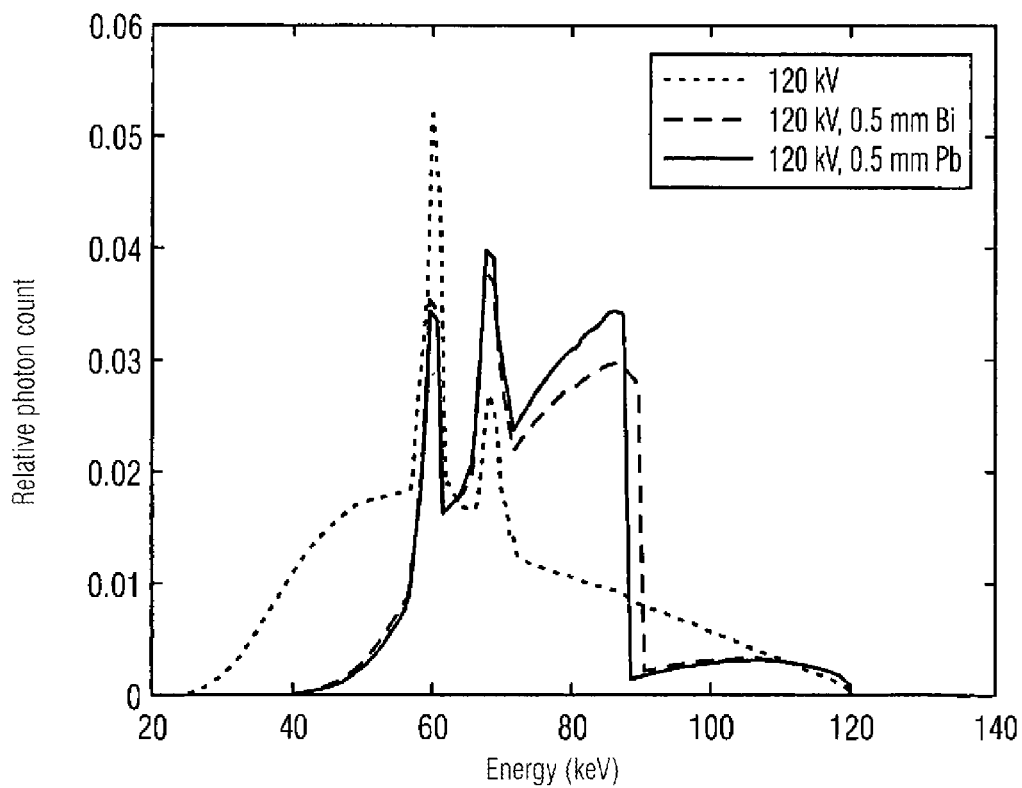
FIG. 2 shows the change in spectral filter characteristics with the filter material. Simulations based on a 120 kV output spectrum and filtration with 0.5 mm bismuth or 0.5 mm lead and 15 cm tissue absorption.
Figure 3:
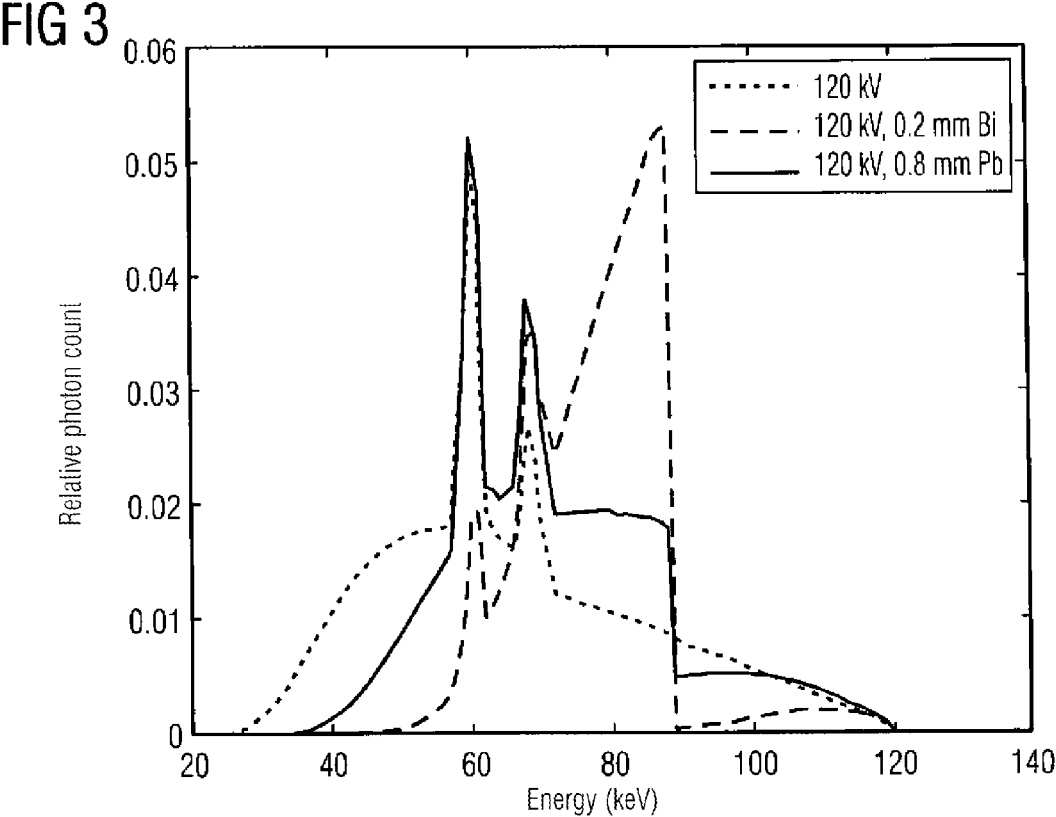
FIG. 3 shows the change in spectral filter characteristics with the thickness of the filter material. Simulations based on a 120 kV output spectrum and filtration with 0.2 mm or 0.8 mm lead and 15 cm tissue absorption.
Figure 4:
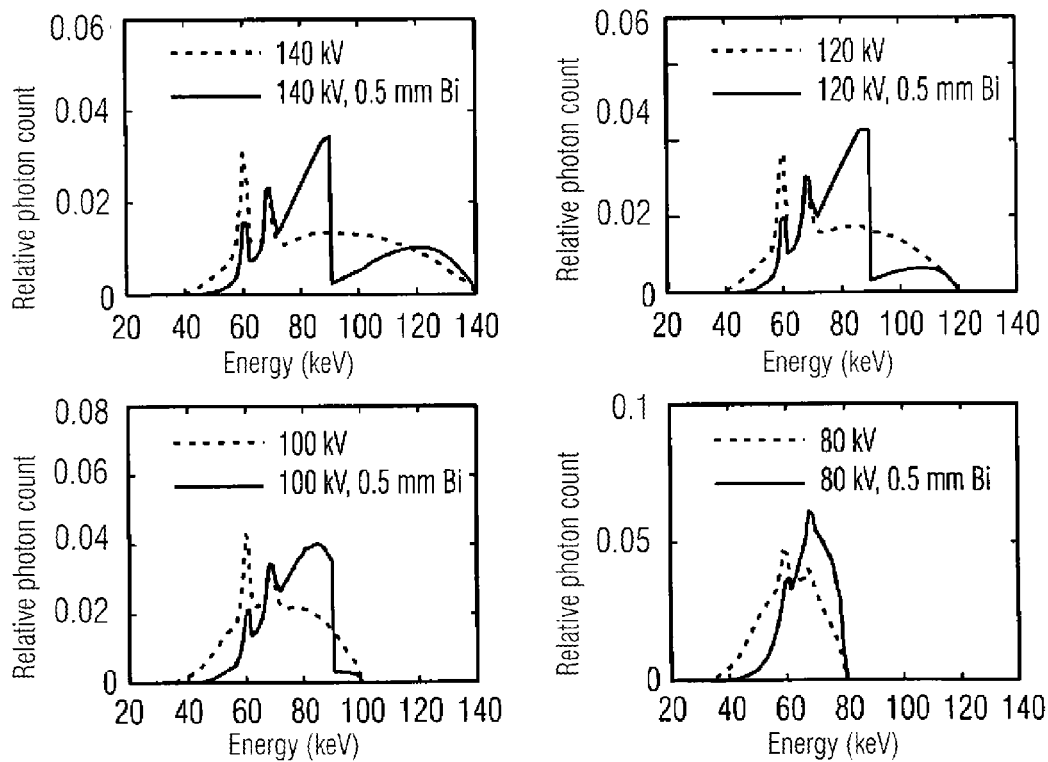
FIG. 4 shows the change in spectral filter characteristics with the tube voltage. Simulations based on output spectra at 140, 120, 100 and 80 kV and filtration with 0.5 mm lead and 15 cm tissue absorption.

The filters, in combination with contrast media of higher atomic number, are the subject matter of an embodiment of the invention. Filters lead fundamentally to an attenuation of the intensity of the radiation and to a reduction in the relative proportion of low-energy photons. The spectral filter characteristic is determined with the filter material (FIG. 2), the filter thickness (FIG. 3) and the selection of the tube voltage (FIG. 4). Optimization of the filter is carried out with regard to the material, thickness and tube voltage to a maximum CNR at a minimum radiation dose. The absorption characteristic of the contrast medium element must be taken into account herein.

Contrast media which are suitable are those which contain one or more elements with an atomic number of 56, in particular one or more elements belonging to the group of lanthanides, for example Lu (Z=71), or in particular the elements hafnium (Z=72), tantalum (Z=73), tungsten (Z=74) or rhenium (Z=75). The use of additional filters and the adjustment thereof to the contrast-creating elements in the contrast medium takes place such that the material of the additional filter has a higher atomic number than the contrast-creating element of the contrast medium and thus the K-edge of the additional filter lies in the range of 5 keV to 40 keV above the K-edge of the contrast-creating element.

Figure 5:
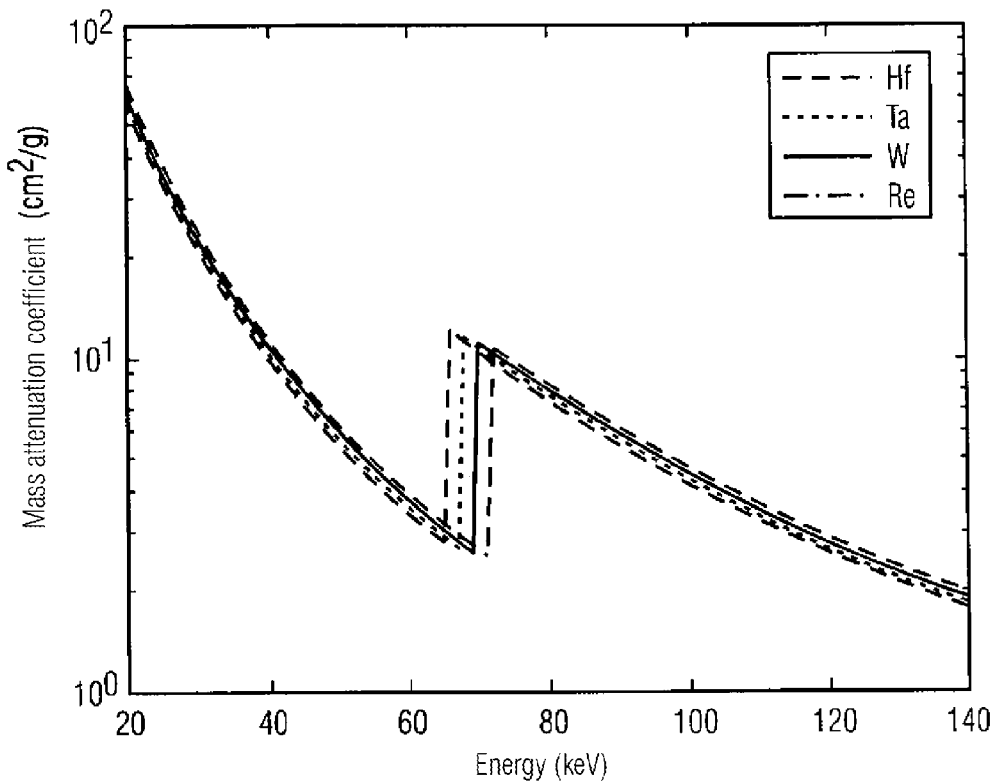
FIG. 5 shows mass attenuation coefficients for the elements hafnium, tantalum, tungsten and rhenium.

Alternatively, however, the use of additional filters and the adjustment thereof to the contrast-creating element in the contrast medium can also be carried out such that the material of the additional filter has a lower atomic number than the contrast-creating element of the contrast medium. Of particular importance, therefore, is the energy of the K-edge at which the attenuation coefficient suddenly rises by a factor of approximately 10 (FIG. 5). The K-edge energy of the contrast-creating element in the contrast medium is in the range of 38.9 keV (La) to 63.3 keV (Lu) for the lanthanides and at around 65.3 keV (Hf), 67.4 keV (Ta), 69.5 keV (W) or 71.7 keV (Re).

Figure 6:
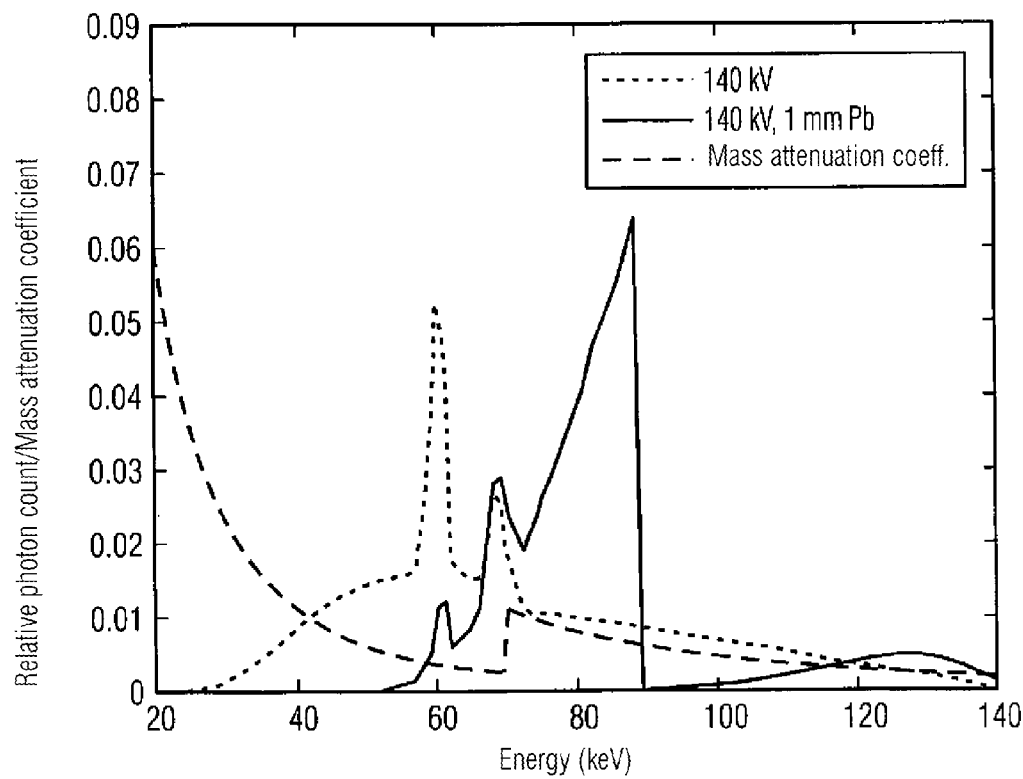
FIG. 6 shows the photon spectrum with and without a lead filter. Simulations based on a 140 kV output spectrum and filtration with 1 mm lead and 15 cm tissue absorption. Shown overlaid is the mass attenuation coefficient for tungsten.

On use of a filter material having a higher K-edge energy than that of the contrast-creating element, the relative proportion of the emitted photons with energies above the K-edge of the contrast medium element is increased. The K-edge energy of the filter material plays a decisive part herein. At this energy, a sudden increase in the photons absorbed in the filter occurs. By this, photons with energies above the K-edge are filtered out of the photon spectrum. The strength of this effect depends on the thickness of the filter (FIG. 3). Ideally, a filter material can have a higher K-edge energy than the contrast medium element since, as a result, the difference range between the K-edges of the contrast medium and of the filter can be increased selectively (FIG. 6).

The K-edge energy increases with the atomic number and the filter materials should therefore have a higher atomic number than the contrast-creating element. Particularly effective is a K-edge energy of the filter material that is higher by an amount in the range of 5 keV to 40 keV. For the lanthanides, in particular Lu and Hf, Ta, W and Re, filters made of lead (K-edge at 88.0 keV) or bismuth (K-edge at 90.5 keV) should be particularly emphasized). Elements with an atomic number of greater than 83 (Bi) are also suitable as filters, but can be used to only a limited extent, due to the radioactivity thereof.

Figure 7:
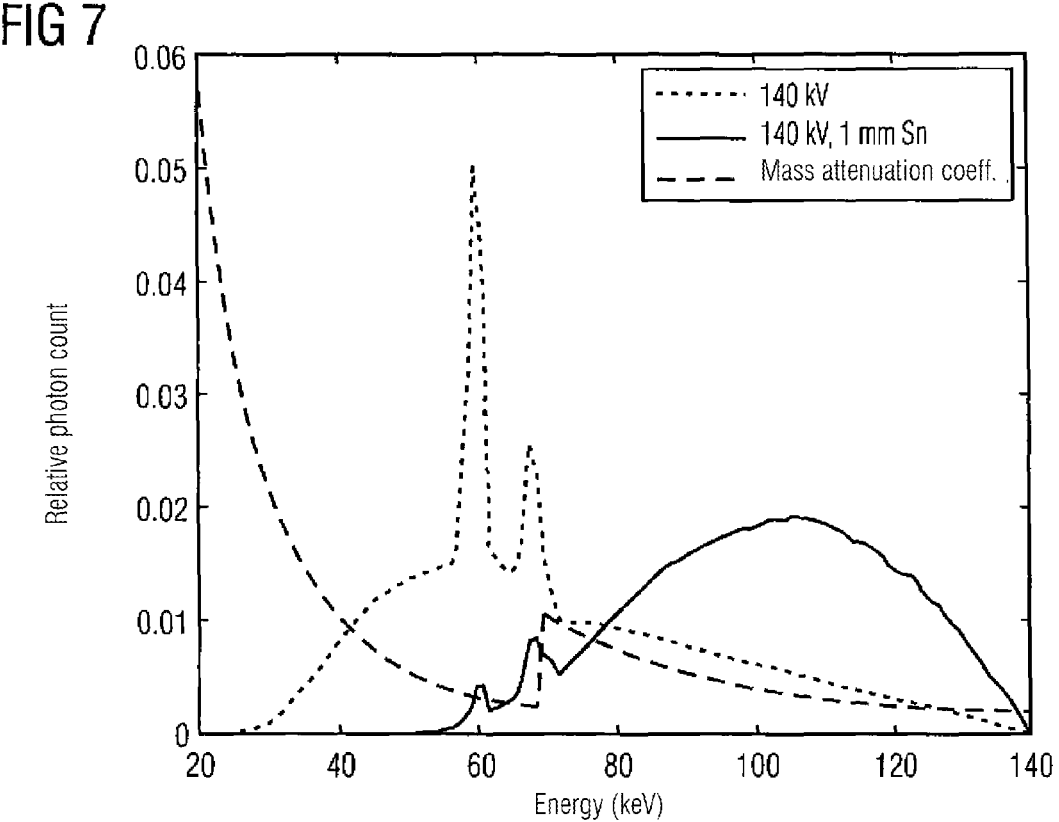
FIG. 7 shows the photon spectrum with and without a tin filter. Simulations based on a 140 kV output spectrum and filtration with 1 mm tin and 15 cm tissue absorption. Shown overlaid is the mass attenuation coefficient for tungsten.

An alternative possibility is the use of filters with a lower atomic number than that of the contrast medium element. These materials lead to a relative increase in the high energy portions, although the enhanced photon energies are, in part, significantly above the optimum absorption range of the contrast medium elements of the lanthanides or of Hf, Ta, W, Re (FIG. 7). A rise in the contrast medium absorption can only be achieved with the filters at low tube voltages <=100 kV.

Physically, by the use of the additional filters described, firstly, the effectiveness (absorption and/or image signal) of the contrast medium can be increased and, secondly, the image noise can be reduced. Increasing the absorption is based on the described adjustment of the photon spectrum to the spectral absorption characteristics of the contrast-creating element. The reduction of image noise is based on reducing the proportion of low-energy photons in the filtered photon spectrum. Both processes contribute to increasing the CNR.

The proportions of individual processes depends on the spectral filter characteristics and thus on the material and the thickness of the filter and the tube voltage used. In order to optimize the photon spectrum for contrast-medium enhanced images, it is possible, in the case of the lanthanides and the elements Hf, Ta, W, Re, to increase the absorption of the contrast medium with additional filters. By contrast thereto, with the currently available iodine-containing contrast media and the voltages >=80 kV used for CT, the absorption always falls off markedly when an additional filter is used (example 1). This marked signal fall-off cannot be compensated for by the aforementioned reduction in image noise, so that the CNR at the same radiation dose is always lower on use of an additional filter, and/or the radiation dose at a constant CNR is always higher (example 1).

In the case of an embodiment of the inventive CT system, the fundamental structure can be a conventional CT system with at least one tube/detector system. However, the system may also be a C-arm or an angiography device. The X-ray tube voltage can cover a range of 60 kV to 160 kV. The detector can be energy-integrating or photon-counting. In addition to the shaped filters currently integrated into CT systems which spatially model the fan-shaped or cone-shaped beam, in the context of the invention, an additional filter is introduced into the beam path (FIG. 8)). This additional filter is fastened to the outlet of the X-ray tube, for example, in the tube protective housing or within the collimator housing. The additional filter is mounted at an angle in the range of 60° to 120°, preferably at right-angles, to the outlet of the beam. The additional filter can be made of one or more materials (metals, alloys). The filter comprises a thin sheet with a thickness in the sub-mm or mm region, or enclosed mercury, and covers at least the diagnostically used cross-section of the beam path.

The additional filter substantially differs, in the spectral filter properties thereof, from the hardening filters conventionally used in CT devices. Automated changing of different filters by way of a technical device is also conceivable. The filter can thus be adapted to different requirements, for example, to normal-weight patients or obese patients. A combination of one filter with one tube voltage can also be advantageous. The filters can differ both in material and in thickness. The selection of a filter is made either manually by the operator or automatically, depending on the planned examination. The volume to be irradiated, the tissue composition and the contrast medium element are the key parameters herein.

Automatic filter selection can be firmly linked to an examination protocol (e.g. angiography of the head) in which the parameter ranges (irradiated volume, tissue composition, contrast medium) are pre-defined for the filter selection. Alternatively, the determination of the suitable filter can also be carried out in a computer-assisted manner, based on a survey view (topogram) in the projection mode or based on optical measuring systems. Using this recording, examination volumes and tissue compositions can be estimated and the relevant filter can be placed in the beam path automatically.

With the tube technology available today, the use of additional filters is substantially restricted to voltages >=120 kV because otherwise the photon flux is not sufficient for high-quality diagnostic imaging. The filter thickness is also limited by the photon flux. Using conventional tube technology and voltages >=120 kV, filter thicknesses of up to a maximum of 1 mm Pb or Bi are practicable. At lower tube voltages, with the present technology the tube output levels are a limiting factor for the use of additional hardening filters. For special applications (e.g. paediatric CT scans) or for future X-ray tubes with an increased photon flux, the use of the aforementioned filters is also possible.

In CT device technology, filters are already in use for spatial and spectral modification of the X-ray radiation. These differ markedly in their purpose and in their spatial and spectral filter characteristics and, in particular in their K-edge energy, from the filters described herein. The shaped filter for spatial modeling is typically made of plastics and has a special geometrical form. The aim of the filter is the spatially resolved modification of the intensity of the photon spectrum. Due to the low mean atomic number, the spectral modification is comparatively small.

The following examples of device and method variants are fundamentally usable within the context of the invention:

The additional filter can be constructed such that the photon energies which are less effective for contrast medium-assisted image contrast creation are absorbed in the filter and therefore the proportion of photon energies which are more effective for the image contrast is increased. The additional filter can be made of one or more metals or an alloy. The additional filter can consist of a thin sheet or enclosed liquid material which can be fastened to a carrier to ensure the mechanical stability thereof. The additional filter can be fastened at an angle, preferably at right-angles, to the emergence of the X-ray beam and spatially close to the X-ray tube, wherein by way of an angular adjustment, the effective filter thickness can be set. The additional filter is to cover the diagnostic beam path completely so that the filter is at least as large as the cross-section of the diagnostic ray path at the location of the filter.

The X-ray system can have a plurality of additional filters, each with different materials and thicknesses which can be brought by at least one electromechanical device into the beam path, depending on the application, particularly for medical indications, for example, CT-angiograms, dynamic contrast medium-assisted CT, by way of a control unit. A plurality of filters can also be used simultaneously.

The selection of the additional filter can be undertaken manually by the operator of the X-ray system, control being carried out computer-aided by way of the operating console.

Selection of the additional filter can be carried out semi-automatically according to the examination protocol, contrast medium or tube voltage selected by the operator. Alternatively, the selection of the filter can be made in a computer-assisted manner by specifying the patient data such as weight, body region or diagnostic objective. Using these data, the selection of the filter is undertaken automatically by the system with software support.

The selection of the filter can be undertaken fully automatically by a computer/control system. The parameters that are relevant for filter selection can be found by an anatomical projection recording along the examination region, based on the measured attenuation values along the body axis or by optical measuring systems. Using these parameters, the selection of the filter is undertaken by the system with software support.

A combination of contrast media and the material and thickness of the additional filter is also proposed such that, in the target region for contrast medium enrichment, a high degree of match is achieved between the energy distribution of the X-ray radiation and the spectral absorption behavior of the contrast-creating element.

The contrast medium can contain one or more elements of relatively high atomic number (Z>56), the lanthanides (lanthanum to lutetium), but in particular the elements rhenium, hafnium, tantalum or tungsten. The energy of the relevant K-edge of the materials is in the range from 38.9 keV to 90.5 keV.

The filter characteristic of the additional filter can be adapted to the spectral absorption behavior of the contrast medium in the examination to be performed in that the filter material, the filter thickness and the tube voltage are modified.

The material of the additional filter can have a higher atomic number than the contrast-creating element of the contrast medium in order thereby to amplify selectively the relative proportion of photons in the energy region between the K-edges of the contrast-creating element and the filter that is particularly effective for image generation. The K-edge of the filter lies in the range of 5 keV to 40 keV above that of the contrast-creating element. This includes, above all, the elements iridium, platinum, gold, mercury, thallium, and in particular lead and bismuth. The K-edge energy of the filter material is, in this case, at least 38.9 keV and particularly effective are K-edge energies of greater than 76 keV.

The material of the additional filter can have a lower atomic number than the contrast-creating element of the contrast medium in order thereby to amplify the proportion of higher-energy photons in the tube spectrum. The atomic number of the filter material in this case is greater than 22 and the corresponding K-edge energy is at least 5 keV.

The additional filter can also comprise a combination of a plurality of elements.

The X-ray system according to an embodiment of the invention and the combination of contrast media of high atomic number with special additional filters increases the contrast-to-noise ratio in the diagnostic X-ray imaging process. This advantage can be utilized to increase the image quality, to reduce the radiation dose to which the patient is exposed or to reduce the contrast medium dose. A combination of these effects is also possible.

Therefore, in order to utilize the potential offered by a K-edge which lies in the range of energies used for X-ray diagnostics, optimization of the pre-filtration of the radiation is also proposed. In this context, it has been recognized that what is important is that the X-ray energies are weighted so as to lie mainly in the region of the K-edge of the contrast medium element. It has also been recognized that elements which have a K-edge which lies above that of the contrast medium are particularly suitable for pre-filtration of this type. The inventors propose as exemplary therefor, the elements iridium, platinum, gold, mercury, lead or bismuth. These elements all have the property, as pre-filtration, of hardening the spectrum of the X-ray beam and thus of utilizing the absorption properties of the K-edge better than with a non-hardened spectrum.

However, X-ray systems such as, for example, CT devices also have other framework conditions that should be taken into account. The user has the possibility of varying the tube voltage. Furthermore, the objects under investigation sometimes differ markedly in diameter and extremes are represented, for example, by pediatric patients and obese patients. Both factors substantially influence the effective spectrum from which the signal is composed in the detector. In the annex, by way of example, CNR2/Dγ curves are shown, simulated as a function of contrast medium, tube voltage, filter thickness and patient thickness. In general, from this series of variables, a selection of contrast medium, tube voltage and patient thickness are specified by the user. The inventors therefore propose that the system itself specifies the filter thickness, using an algorithm, depending on the other parameters. A wide variety of versions is possible:
1. The system simulates the given parameters and determines therefrom the optimum filter thickness.
2. Tables in which the optimum filter thickness is shown depending on the input variables are stored in the system. From this, the system determines the optimum filter thickness.

An embodiment of the invention therefore includes a system wherein different filters with different filter thicknesses of the same material are available and movable in the collimator housing. Alternatively, a plurality of filters made of different materials can be combined in a system.

It is also possible for the system, within the scope of the filter possibilities thereof, to propose to the user which contrast medium results in an optimum dose utilization at which voltage for a given patient diameter.

Also included within the scope of an embodiment of the invention are:

use in CT angiography for reducing the radiation dose received by the patient;

use in CT angiography for increasing the image quality and thus the diagnostic validity, particularly in coronary angiography and in angiography for small and peripheral vessels;

use in dynamic contrast medium-assisted CT imaging, for example, multi-phase liver diagnostics, brain perfusion, tumor perfusion or myocardial perfusion for reducing the radiation dose received by the patient;

use in dynamic contrast medium-assisted CT imaging, for example, multi-phase liver diagnostics, brain perfusion, tumor perfusion or myocardial perfusion, for increasing image quality and thus the accuracy of the functional parameters derived therefrom;

use in contrast medium-assisted CT tumor diagnostics for reducing the radiation dose received by the patient;

use in contrast medium-assisted CT tumor diagnostics for increasing image quality and thus the diagnostic validity;

use in contrast medium-assisted CT imaging for reducing the contrast medium dose, in particular for renal insufficiency patients or patients with contrast medium intolerance; and use in which one or more contrast media with different atomic numbers are applied simultaneously or in sequence for use in a dual energy CT examination of a patient.

Based on the basic concept of an embodiment of the invention described above, the inventors propose the following:

A method for generating at least one X-ray image of a patient with incorporated contrast medium, using X-ray radiation generated at an anode and having an energy spectrum of bremsstrahlung and characteristic radiation, and an X-ray detector, wherein the energy spectrum used is modified by at least one first filter arranged in the beam path in front of the patient, the patient absorbs a dose in order to generate detector data for the X-ray image and the X-ray image has a CNR value which represents the ratio of the maximum contrast in the object under investigation to the noise, wherein, according to the invention, taking account of the thickness of the patient to be X-rayed, the energy spectrum and the contrast medium are adjusted to one another by an additional filter such that an optimization criterion taken from an experimentally generated or simulated X-ray image, is maximized.

It should be noted that the expression "first filter" is used to mean a beam hardening filter firmly arranged in or at the X-ray tube and serving to meet the legal requirements regarding the absorption of low-energy X-ray radiation that is not suitable for imaging a patient because the low energy radiation is absorbed in low layer thicknesses. A filter of this type can also be combined, for example, with the vacuum window of the X-ray tube. The expression "additional filter" denotes at least one additional filter element which can be introduced into or removed from the beam path as needed in order to optimize the X-ray spectrum of the radiation in front of the patient according to the criteria described herein.

For the optimization criterion, the ratio ($CNR^2/D\gamma$) of the square of the contrast-to-noise ratio ($CNR^2$) of the X-ray image of the patient to the dose ($D\gamma$) received by the patient for this X-ray image can be maximized.

Alternatively or additionally, for the optimization criterion, the ratio (CNR/DK) of the contrast-to-noise ratio (CNR) of the X-ray image of the patient to the incorporated contrast medium dose (DK) can be maximized.

Where both optimization criteria are used in relation to radiation dose and contrast medium dose, both optimization criteria can be combined, normalized for the most comparable possible effects as a product, for example, the product $CNR^2/(D\gamma/D\gamma(norm))*CNR/(DK/DK(norm))$ of the two normalized optimization criteria. The normalization variables $D\gamma(norm)$ and $DK(norm)$ are herein selected such that a weighing up of benefit and risk is carried out for both doses. For example, $D\gamma(norm)$ can correspond to a reference value of the dose for diagnostic and interventional X-ray examination according to §16(1), sentence 3 RöV (German X-Ray Regulations) and DK(norm) to the recommended maximum dose from the specialist information (package information sheet) of the respective contrast medium. This therefore means that, rather than the aforementioned optimization criteria related, in each case, to a dose, the aforementioned product of both optimization criteria can be set and thus belongs within the scope of an embodiment of the invention, and can be applied in combination with the method described below.

Also proposed is the use of a combination of predominantly absorbent material for the additional filter and predominantly contrast-creating material for the contrast medium such that the K-edge of the absorbent material of the additional filter lies energetically above the predominantly contrast-creating material of the contrast medium.

Based on an embodiment of the aforementioned method, it is also proposed that the method is to be carried out automatically or semi-automatically to the extent that both non-adjustable and adjustable recording parameters are defined for the examination, wherein at least one parameter from the following list is taken as a non-adjustable recording parameter: patient diameter, contrast medium dose, material or element of the contrast medium, pre-determined patient dose to be applied, CNR. As a variable recording parameter, at least one of the parameters from the following list can be used, provided the parameter has not been selected as a non-adjustable recording parameter: maximum photon energy, anode material, material of the additional filter, thickness of the additional filter, material or element of the contrast medium, contrast medium dose, patient dose to be applied, CNR. The user of the inventive method can therefore be enabled, by simple means, taking account of the given circumstances, to carry out optimized adjustment of the recording parameters of the X-ray system.

The inventors also propose that the maximization of the optimization criterion should be made so that the following method steps are performed:

determining the mean thickness of the patient in the region to be recorded, introducing test results, for example, from simulations, phantom tests or based on experimental values, from recordings with a plurality of different energy spectra taking account of the mean thickness of the patient and determination of associated CNR values between contrast medium-free tissue and contrast medium-enriched body fluid or tissue or between maximum and minimum image values from the overall image of the patient, selecting a configuration of energy spectrum and contrast medium with a maximum value for the optimization criterion, setting this selected configuration, and generating at least one projection of the patient using the selected configuration.

It may also be favorable, taking account of the mean thickness of the patient in the recording region to test only configurations of maximum energy of the energy spectrum, additional filter material and contrast medium used, wherein:

the K-edges of the additional filter material lie between the maximum of the bremsstrahlung spectrum without additional filters and the maximum energy of the energy spectrum, and the K-edges of the contrast medium lie between the maximum of the bremsstrahlung spectrum without additional filters and the K-edges of the additional filter material.

In order to vary the energy spectrum for the tests to be performed and the test results produced, the maximum energy of the energy spectrum—which is determined from the acceleration voltage applied between the anode and the cathode of the X-ray tube or from the maximum energy of the electrons which generate the bremsstrahlung on entering the anode material—can be varied.

Furthermore, the energy spectrum can also be varied by variation of the anode material, since the atomic number of the anode material and the electron levels of the electron shells of the material used which are present in the anode material and the resulting absorption edges, predominantly the K-edges, determine the X-ray spectrum emitted from the anode.

Furthermore, in order to vary the energy spectrum for the test results, the layer thickness of at least one additional filter in the beam path in front of the patient can be varied.

Furthermore, in order to vary the energy spectrum for the test results, the material of at least one additional filter in the beam path in front of the patient can be varied, wherein preferably the material of the additional filter overwhelmingly consists of at least one of the materials with an atomic number greater than 22, in particular from the following list or a combination of a plurality of materials from the following list: iridium (atomic number $Z=77$), platinum ($Z=78$), gold ($Z=79$), mercury ($Z=80$), lead ($Z=82$), bismuth ($Z=83$).

In the search for an optimum mutual adaptation between the energy spectrum of the X-ray radiation used and the absorption spectrum of the contrast medium used, it is further proposed that the contrast-creating materials varied for the test results should be used in the contrast medium. As the contrast-creating materials in the contrast medium materials or material combinations from the following list can preferably be used: rhenium (atomic number $Z=75$), hafnium ($Z=72$), tantalum ($Z=73$), tungsten ($Z=74$). This list of materials can also include elements from the group of lanthanides (atomic number $Z=58$ to $71$).

In the method according to an embodiment of the invention, for the X-ray imaging of the patient, a projective X-ray image, a sinogram from a CT scan or a two-dimensional or a three-dimensional tomographic image representation can be used.

In the context of a CT scan, the mean thickness of the patient in the recording region can also be determined by creating at least one topogram, at least in the recording region from at least one projection direction.

Alternatively, it is also possible for the mean thickness of the patient in the recording region to be determined by optical scanning, for example a laser scan or at least one optical recording, at least in the recording region.

It is also possible to estimate the mean thickness of the patient in the recording region based on weight, height and optionally sex data.

In addition to the aforementioned methods, the inventors also propose a method of an embodiment for recording X-ray images in the combination of an X-ray system with contrast media, wherein the contrast medium contains the elements rhenium, hafnium, tantalum or tungsten, wherein the contrast-to-noise ratio between the contrast medium-accumulating tissues and the surrounding tissue is increased and at least one additional filter with at least one element with the atomic numbers 77 (iridium), 78 (platinum), 79 (gold), 80 (mercury), 82 (lead) or 83 (bismuth) is introduced in front of the X-ray tube into the beam path and the radiation emitted by the X-ray tube is thereby modified spectrally.

The inventors also propose, in at least one embodiment, a method for recording X-ray images in combination with an X-ray system with contrast media, wherein the contrast medium contains at least one of the elements rhenium, hafnium, tantalum or tungsten, and at least one additional filter is provided in which at least one of the elements with the atomic numbers 77 (iridium), 78 (platinum), 79 (gold), 80 (mercury), 82 (lead) or 83 (bismuth) is used, and the at least one additional filter is introduced into the beam path between the X-ray tube and the patient in order to modify the radiation emitted by the X-ray tube spectrally, wherein computer-assisted tomographic images are reconstructed and the increase in the image contrast is used, alongside the rise in image quality, to reduce the radiation dose or the contrast medium dose.

The two latter methods can be used, in particular, in conjunction with CT angiography, dynamic contrast medium-assisted CT or a contrast medium-assisted CT tumor diagnostic technique.

In addition to an embodiment of the inventive method, an X-ray system for generating at least one X-ray image of a patient with incorporated contrast medium is proposed, comprising:

at least one anode for generating X-ray radiation with an energy spectrum of bremsstrahlung and characteristic radiation, at least one X-ray detector for pixel-wise measurement of the X-ray radiation penetrating the patient, at least one filter arranged in the beam path between the at least one anode and the at least one X-ray detector, which is placed in front of the patient and which modifies the energy spectrum used, wherein the patient absorbs a dose in order to generate detector data for the X-ray image and the X-ray image has a CNR value which represents the ratio of the maximum contrast between tissue enhanced by contrast medium and the surrounding tissues in the image, to the noise, at least one computer processor having at least one memory store in which computer programs with calculation and control instructions for execution are stored which control the X-ray system during operation and generate X-ray images from the received detector data, wherein, according to the invention at least one computer program is stored which carries out the method steps of one of the above methods during operation.

The X-ray system may be, for example, a C-arm system, a computed tomography system or a system for generating exclusively projectional X-ray images.

An embodiment of the invention also relates to the use of one of the X-ray systems described above:

in CT angiography for reducing the radiation dose received by the patient;

in CT angiography for increasing the image quality and thus the diagnostic validity, particularly in coronary angiography and in angiography for small and peripheral vessels;

in dynamic contrast medium-assisted CT imaging, for example, multi-phase liver diagnostics, brain perfusion, tumor perfusion or myocardial perfusion for reducing the radiation dose received by the patient;

in dynamic contrast medium-assisted CT imaging, for example, multi-phase liver diagnostics, brain perfusion, tumor perfusion or myocardial perfusion, for increasing image quality and thus the accuracy of the functional parameters derived therefrom;

in contrast medium-assisted CT tumor diagnostics for reducing the radiation dose received by the patient;

in contrast medium-assisted CT tumor diagnostics for increasing image quality and thereby the diagnostic validity;

in contrast medium-assisted CT imaging for reducing the contrast medium dose, in particular for renal insufficiency patients or patients with contrast medium intolerance;

in a dual energy CT examination of a patient, wherein the patient has one or more contrast media with different atomic numbers simultaneously or sequentially.

FIGS. 1 to 7 show example typical X-ray spectra and the influence of differing filtration with additional filters made of different filter materials on the X-ray spectra, with the possibility of targeted amplification of the essential imaging radiation components in restricted energy regions in which optimally selected contrast medium elements show maximum absorption.

Figure 8:
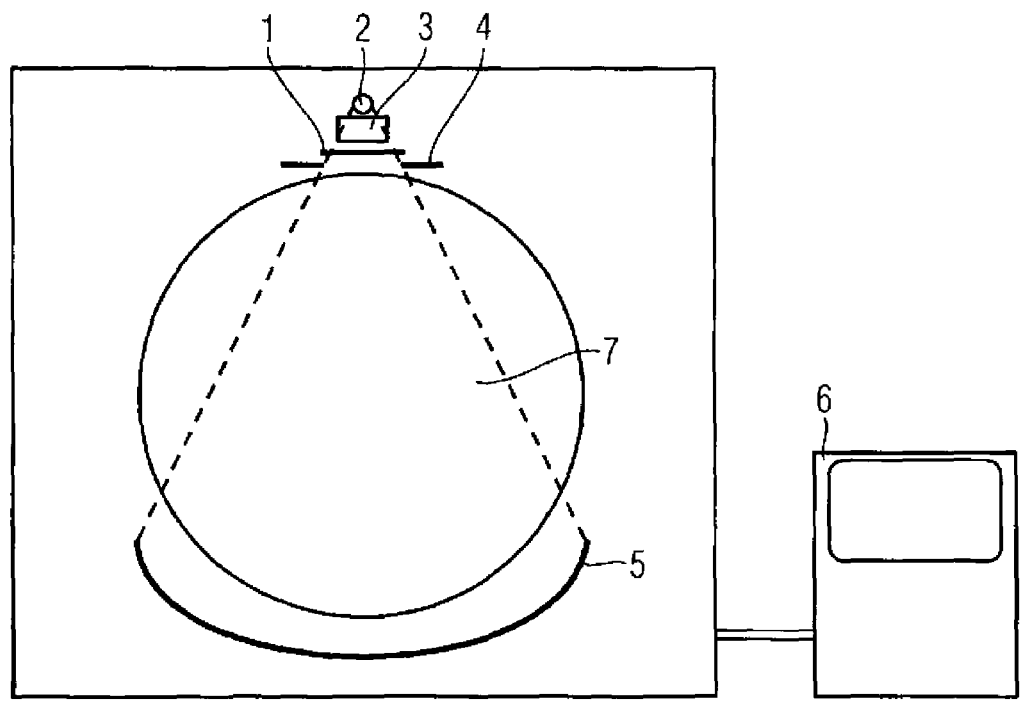
FIG. 8 is a schematic representation of a CT system with an X-ray source and a detector.

A typical construction of an inventive X-ray system is shown in FIG. 8. This X-ray system has an X-ray tube with a focus 2 on an anode, from which X-ray radiation is emitted along a beam path 7. This X-ray radiation initially passes through a shaping filter 3 and is subsequently spectrally modified by a variable additional filter 1 and directed to a limited extent by collimators 4 onto a detector 5. Situated in the radiation beam 7 on execution of the method is a patient (not shown in detail here) with incorporated contrast medium so that with the aid of the detector 5, the absorption characteristics of the patient can be measured. In order to vary the additional filter, for example, filter layers of different thickness or different filter materials can be used. Control of the X-ray system including the inventive optimization processes and the input or determination of unchangeable examination parameters as well as the output of proposals for optimized adjustment parameters or automatic selection and adjustment thereof can be carried out with the control and computer system 6.

Figure 9A:
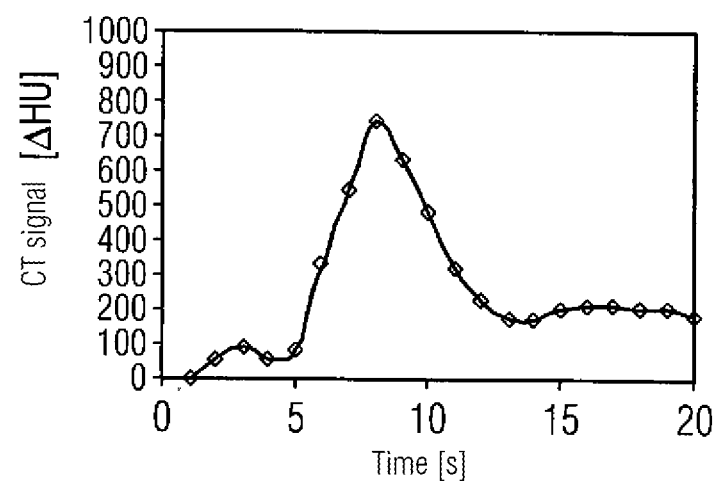
FIGS. 9A-9D relate to a contrast medium-assisted CT examination of a rat with a tungsten-containing substance: without any additional filter (FIGS. 9A, 9B) and with additional filtration with 0.25 mm lead (FIGS. 9C, 9D); time-signal curve measured in the aorta (FIGS. 9A, 9C); CT recording at the peak of a contrast medium bolus (FIGS. 9B, 9D).
Figure 9B:
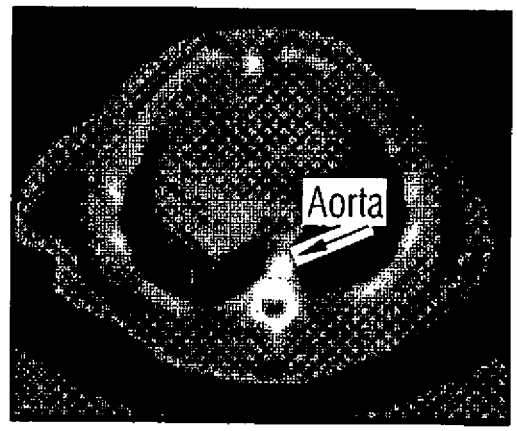
Figure 9C:
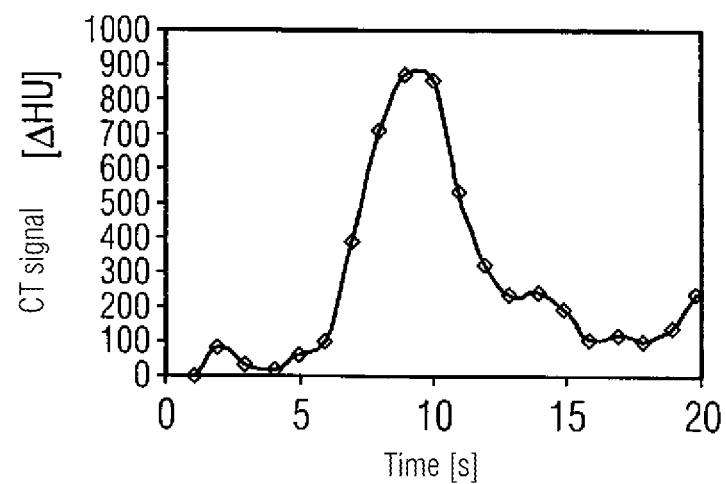
Figure 9D:
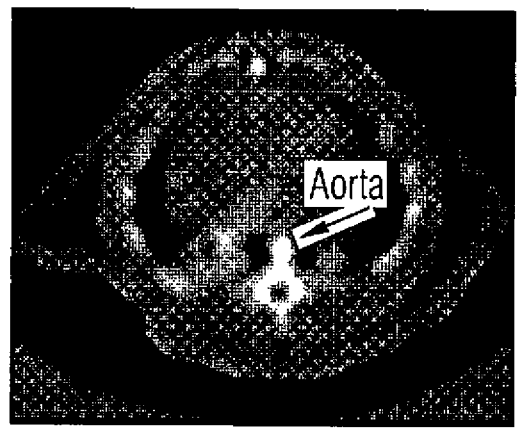
Figure 10:
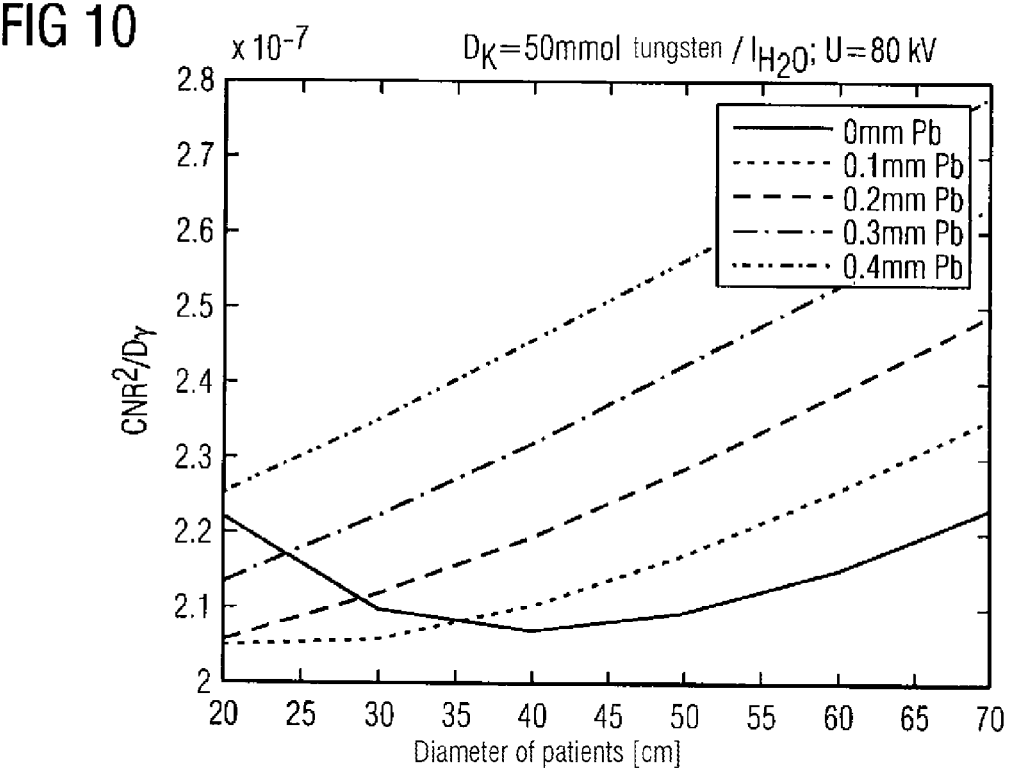
FIGS. 10-13 are representations of the change in the optimization variable $CNR^2/D\gamma$ for the contrast media iodine and tungsten at different thicknesses of the additional filter made of lead.
Figure 11:
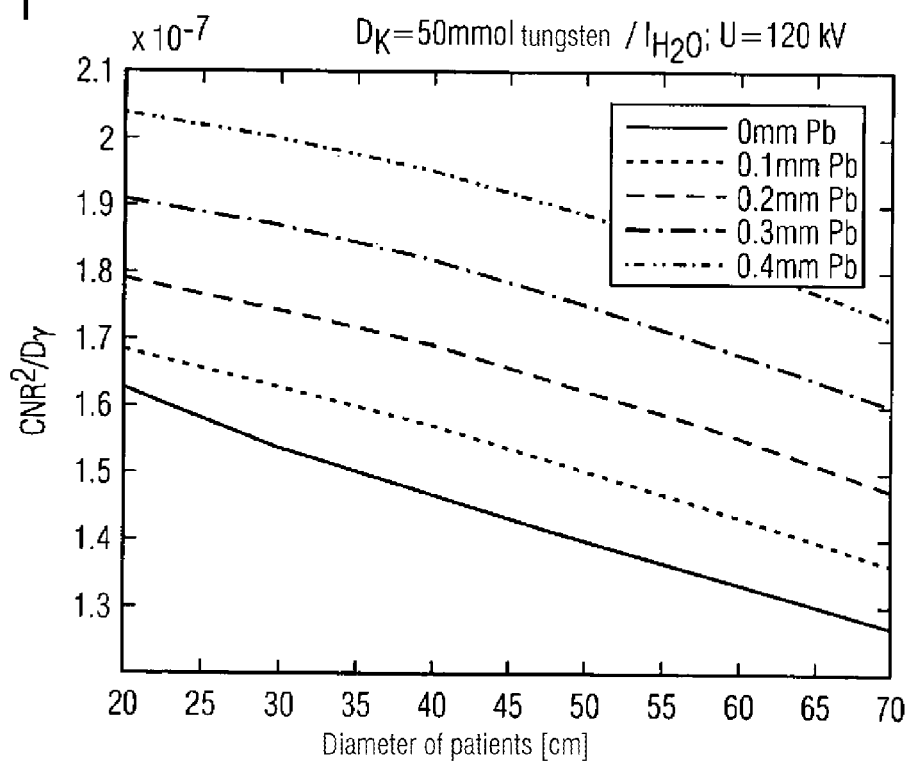
Figure 12:
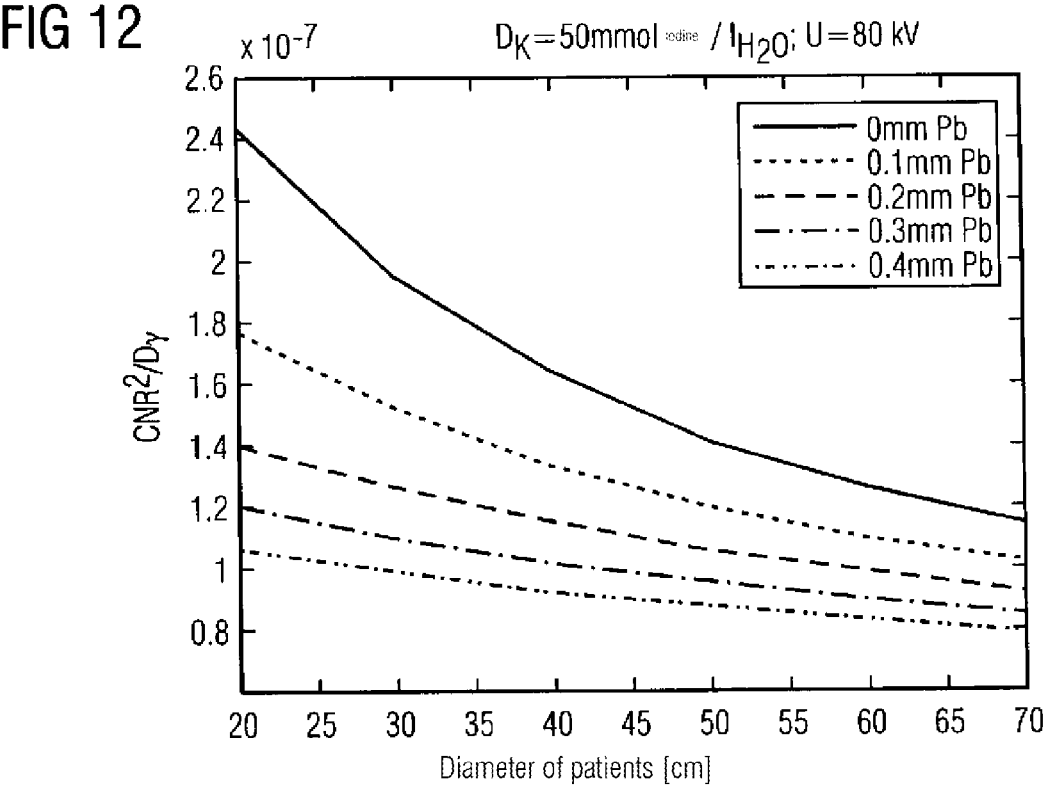
Figure 13:
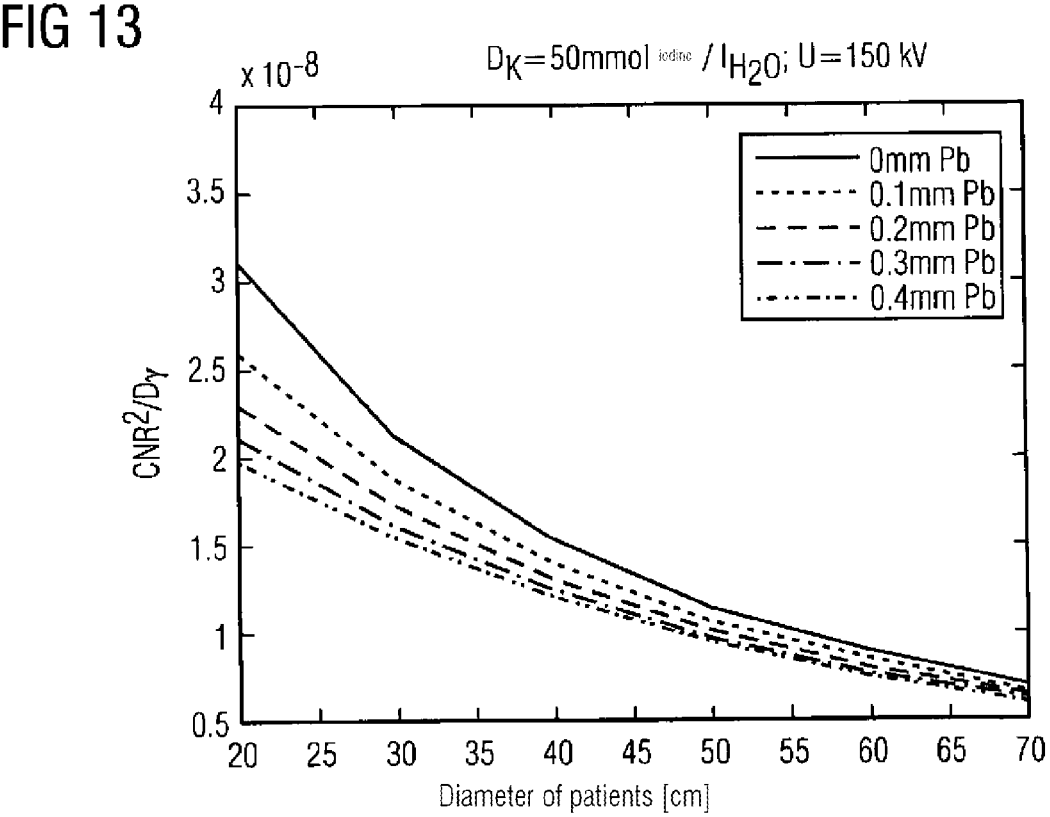

FIGS. 9A to 9D show a contrast medium-assisted CT examination according to example 2 outlined below in the rat with a tungsten-containing contrast medium, wherein FIGS. 9A and 9B represent a CT signal shape or a CT recording without additional filters and FIGS. 9C and 9D show a CT signal shape or a CT recording with additional 0.25 mm lead filtration. FIGS. 9A and 9C show the change of the CT signal over time in CT values normalized according to Hounsfield (HU) in the aorta and FIGS. 9B and 9D each show a CT recording at the peak of the contrast medium bolus.

FIGS. 10 to 13 show, for better understanding of the invention, the ratio of noise to radiation dose ($CNR^2/D\gamma$), which is to be optimized, at a pre-determined dose of contrast medium based on tungsten (FIGS. 10 and 11) and based on iodine (FIGS. 12 and 13) with varying thicknesses of the additional filter made of lead at different accelerating voltages U and with different patient thicknesses, in this case measuring using a water-filled phantom. In each of these phantom measurements, a contrast medium concentration DK of 50 mmol contrast medium per liter of water is used in the phantom at an acceleration voltage U in the range of 80 kV to 150 kV. It is readily apparent that the optimum of the $CNR^2/D\gamma$ value does not follow any simple relation and depends on the acceleration voltage used, the contrast medium, the filtration and the patient thickness, and the combination of these factors with one another.

Figure 14:
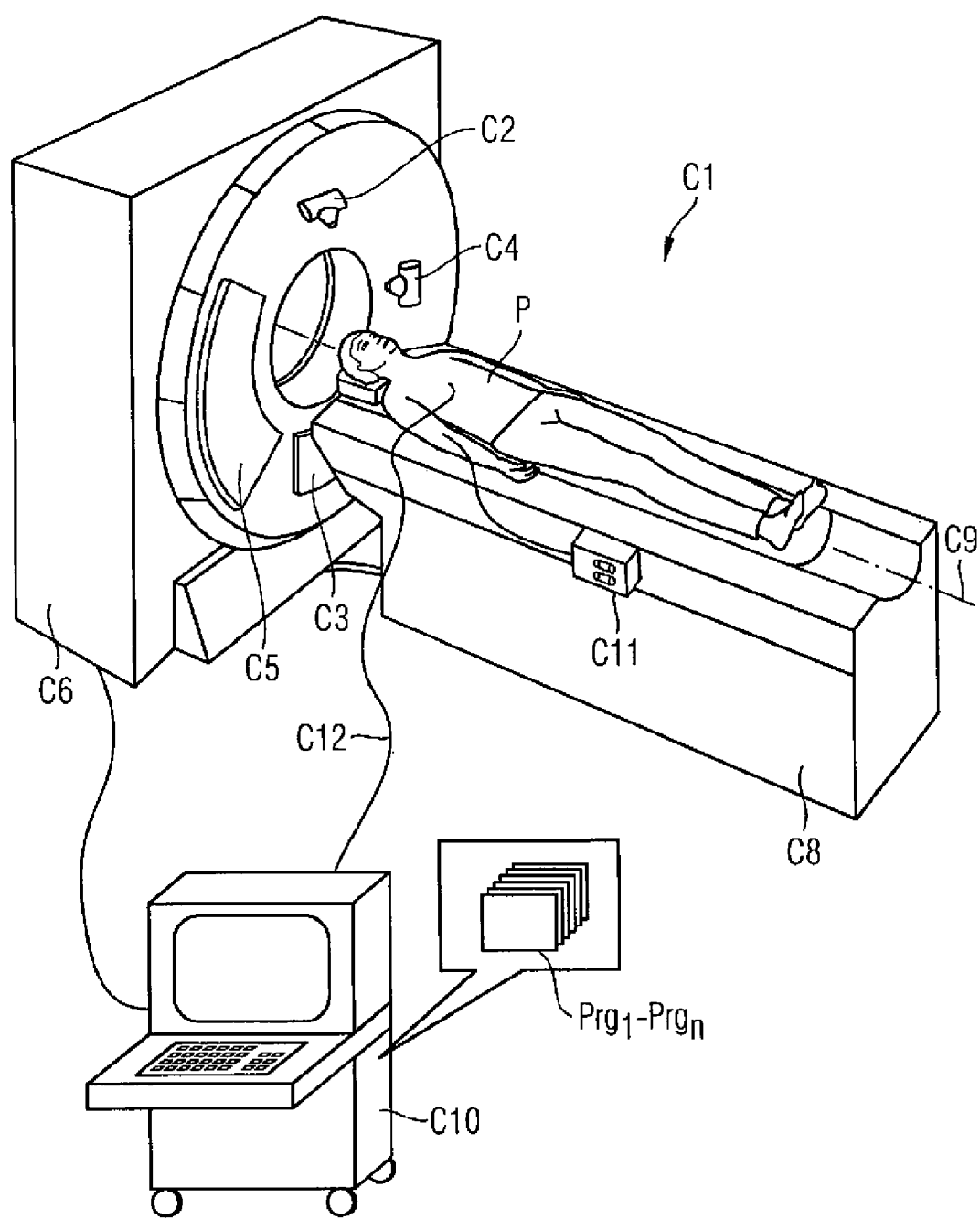
FIG. 14 is a schematic representation of a CT system having two emitter/detector systems.

FIG. 14 shows an X-ray system in the configuration of a CT system C1 for using an embodiment of the inventive method, in particular by carrying out the computer programs Prg1-Prgn on a control and computer system C10 during operation of the CT system C1. The CT system C1 in the embodiment shown here comprises a gantry housing C6 with arranged therein, integrated on the gantry, two emitter-detector systems, each consisting of an X-ray tube C2 and C4 with, in each case, a detector C3 and C5 arranged opposing the X-ray tubes. For scanning, a patient P is moved with the aid of a patient support C8, by intervals or continuously, along the system axis C9 through the beam paths of the two emitter-detector systems and is thereby scanned. For this purpose, firstly, the thickness of the patient can be determined in the scanning region and, based on this thickness and on previous tests with phantoms or on previously performed simulations or on existing real scan results, an optimum combination of incorporated contrast medium and radiation spectrum to be used can be selected. The radiation spectrum created at the focus is modified by suitable selection of additional filters C2.1 or C4.1, which are inserted between the emitter and the patient in the beam path, such that the spectral center point of the X-ray spectrum is optimally adapted to the absorption maximum of the contrast medium used. The incorporation of contrast medium into the patient can be carried out, for example, by automatic application with the contrast medium applicator C11.

In a particularly favorable embodiment of the X-ray system, the variation of the additional filter C2.1 and C4.1 can be performed with the aid of filters of different thicknesses and different materials, which are automatically moved in and out.

Figure 15:
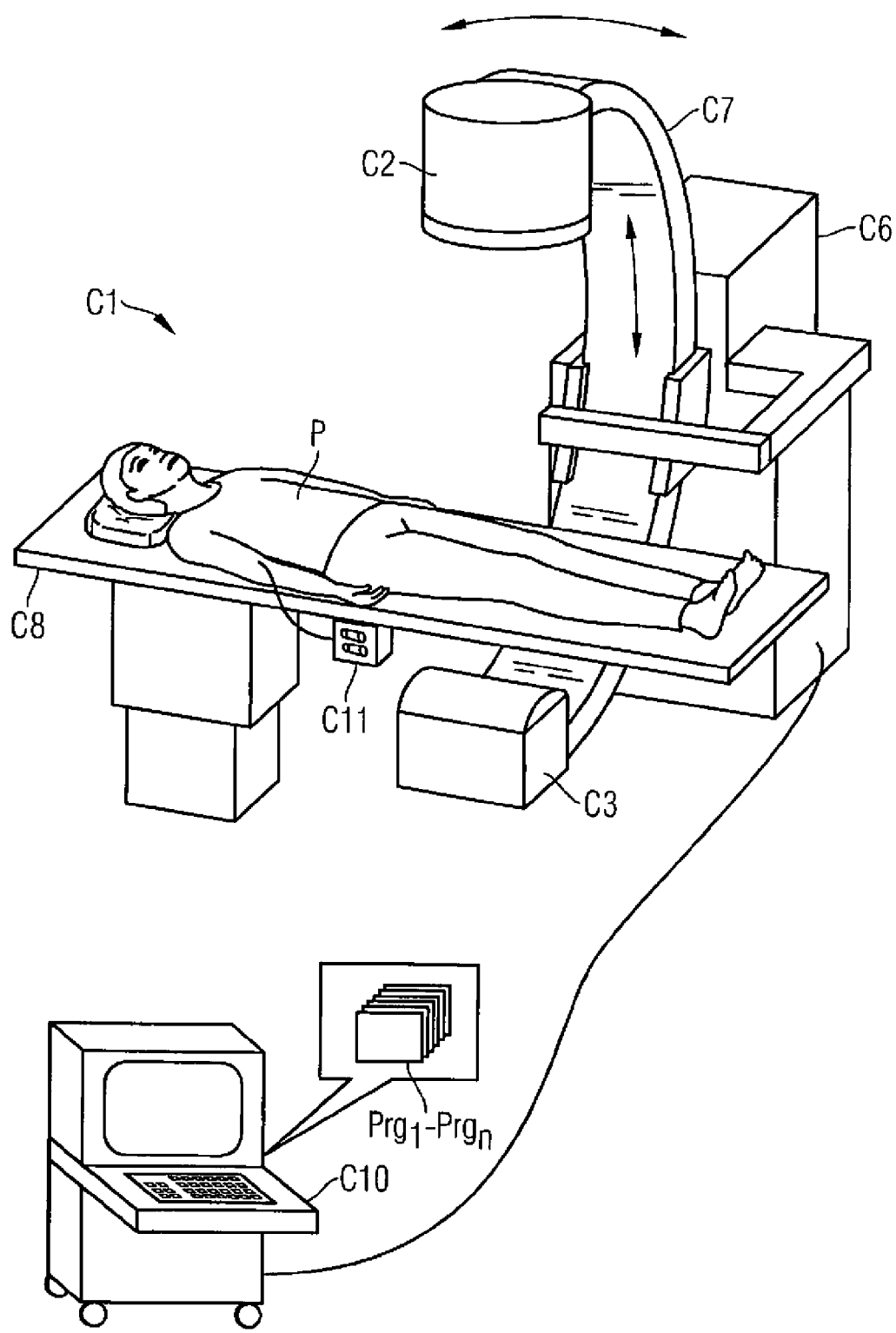
FIG. 15 is a schematic representation of a C-arm system with one X-ray source and one detector.

Alternatively, a C-arm system C1 can be used as the X-ray system, as shown in FIG. 15. The system has a housing C6 to which a movable C-arm C7 is linked. Arranged at the ends of the C-arm C7 are an X-ray tube C2 and, opposed thereto, a flat detector C3. Mounted in front of the X-ray tube C2 is an additional filter system C2.1 in which different additional filters can be introduced into the beam path under automatic control with the aid of a revolver system. For the examination, the C-arm C7 is arranged such that the patient P placed on the patient support C8 is situated in the beam path and can be scanned. Alternatively, the C-arm can execute a pivot motion during scanning so that projections can be recorded from a large number of projection angles and a tomographic image reconstruction can be carried out. In this case, also the contrast medium can be incorporated by way of a contrast medium applicator C11. The necessary calculations and the control of the system are performed with the control and computer system C10 by running the computer programs Prg1-Prgn during operation of the system.

EXAMPLES

Example 1

In Vitro Measurements

A clinical CT device (Siemens Volume Zoom, from Siemens Healthcare, Erlangen, Germany) was equipped with an additional filter of various materials (Pb, Sn) and filter thicknesses (0.25 mm, 0.5 mm, 0.7 mm). These filters had been made of metal films (Goodfellow GmbH, Bad Neuheim, Germany) at the relevant thicknesses and were fastened between two thin plastics carriers in the collimator housing. The beam path was completely covered in this way so that only filtered radiation was emitted. The CT device could thus be used without restriction for imaging. The experimental conditions were adapted as realistically as possible to a patient examination. In order to simulate a patient, an anthropomorphic abdominal phantom (from QRM GmbH, Mohrendorf, Germany) made of tissue-equivalent plastics material was used. Tungsten and iodine contrast medium samples (10 mgX/ml) placed in the relevant inserts of the phantom were used to represent contrast medium-accumulating tissue. A water sample served as a reference. Table B1 shows the HU values for tungsten determined in relation to water with different additional filters. In the case of lead filtration, an increase in the HU values was measured at all tube voltages, whilst with Sn filtration, an increase was measured only at 80 kV.

TABLE B1

CT signals in Hounsfield units [ΔHU] for a tungsten contrast medium sample without (0 mm) and with additional filters (0.25 mm Pb, 0.5 mm Pb, 0.5 mm Sn, 0.7 mm Sn) at 80, 120 and 140 kV.

| Voltage | CT absorption [ΔHU] for tungsten (10 mg/ml) | | | | |
|---|---|---|---|---|---|
| [kV] | 0 mm | 0.25 mm Pb | 0.5 mm Pb | 0.5 mm Sn | 0.7 mm Sn |
| 80 | 298 | 309 | 347 | 332 | 354 |
| 120 | 308 | 336 | 316 | 305 | 301 |
| 140 | 281 | 293 | 326 | 257 | 249 |

Table B2 shows the HU values determined in relation to water for iodine, with different additional filters. The use of additional filters always leads to a decrease in the HU values.

TABLE B2

CT signals in Hounsfield units [ΔHU] for an iodine contrast medium sample without (0 mm) and with additional filters (0.25 mm Pb, 0.5 mm Pb, 0.5 mm Sn, 0.7 mm Sn) at 80, 120 and 140 kV.

| Voltage | CT absorption [ΔHU] for iodine (10 mg/ml) | | | | |
|---|---|---|---|---|---|
| [kV] | 0 mm | 0.25 mm Pb | 0.5 mm Pb | 0.5 mm Sn | 0.7 mm Sn |
| 80 | 424 | 336 | 296 | 316 | 301 |
| 120 | 251 | 224 | 225 | 159 | 142 |
| 140 | 208 | 181 | 180 | 125 | 112 |

On use of a lead additional filter, an increase in the absorption of tungsten by 9.2%/2.7% (120 kV) and 4.4%/15.9% (140 kV) Hounsfield units (HU) at filter thicknesses of 0.25 mm and 0.5 mm Pb, respectively, as compared with measurement without additional filters, was determined. At the same time, the iodine signal decreased by 10.7%/10.3% (120 kV) and 12.9%/13.5% (140 kV) at filter thicknesses of 0.25 mm and 0.5 mm, respectively. At 80 kV, an increase in the tungsten HU by 3.6% (0.25 mm Pb), 16.4% (0.5 mm Pb), 11.30% (0.5 mm Sn) and 18.8% (0.7 mm Sn) was observed. The iodine signal decreased by 20.6% (0.25 mm Pb), 30.0% (0.5 mm Pb), 25.4% (0.5 mm Sn) and 28.9% (0.7 mm Sn).

Apart from the increase in the absorption of X-ray radiation by the contrast medium, the use of additional filters leads to a decrease in the radiation dose received. The radiation dose was determined with an ionization chamber (PTW 31010 from PTW, Freiburg, Germany) calibrated to the water energy dose. For this purpose, the chamber was placed in the insert of the phantom and the relevant image noise in the reconstructed CT images was determined. The image noise was determined via the standard deviation of a homogeneous region (phantom or contrast medium sample). With an identical radiation dose, the use of an additional filter leads to a decrease in the noise level. This effect is independent of the tube voltage. With an identical radiation dose, reductions in the image noise by 11.4% (0.25 mm Pb), 3% (0.5 mm Pb), 15.5% (0.5 mm Sn) and 16.3% (0.7 mm Sn) were determined.

The CNR-to-dose ratio for all the filters used was determined from the absorption data and the dose measurements. Compared with the measurements without additional filters, for tungsten, an increase in the CNR-to-dose ratio was determined, with the exception of the combination 120 kV/0.5 mm Pb. This rise can be used to reduce the radiation dose for identical image quality (CNR). Table B3 shows the relative radiation dose necessary therefor. At 120 kV and 0.25 mm Pb filtration, an identical CNR can be achieved at 66% of the radiation dose without additional filtration.

TABLE B3

Relative radiation dose at constant CNR for a tungsten contrast medium sample without (0 mm) and with additional filters (0.25 mm Pb, 0.5 mm Pb, 0.5 mm Sn, 0.7 mm Sn) at 80, 120 and 140 kV.

| Voltage | Relative radiation dose for tungsten (CNR constant) | | | | |
|---|---|---|---|---|---|
| [kV] | 0 mm | 0.25 mm Pb | 0.5 mm Pb | 0.5 mm Sn | 0.7 mm Sn |
| 80 | 1 | 0.80 | 0.79 | 0.65 | 0.54 |
| 120 | 1 | 0.66 | 1.03 | 0.83 | 0.82 |
| 140 | 1 | 0.73 | 0.71 | 0.99 | 1.00 |

For iodine-containing contrast medium, however, the radiation dose increases when additional filters are used. Table B4 shows the relative radiation dose necessary for an identical CNR.

TABLE B4

Relative radiation dose at constant CNR for an iodine contrast medium sample without (0 mm) and with additional filters (0.25 mm Pb, 0.5 mm Pb, 0.5 mm Sn, 0.7 mm Sn) at 80, 120 and 140 kV.

| Voltage | Relative radiation dose for iodine (CNR constant) | | | | |
|---|---|---|---|---|---|
| [kV] | 0 mm | 0.25 mm Pb | 0.5 mm Pb | 0.5 mm Sn | 0.7 mm Sn |
| 80 | 1 | 1.38 | 2.39 | 1.52 | 1.63 |
| 120 | 1 | 1.09 | 1.54 | 2.84 | 4.05 |
| 140 | 1 | 1.18 | 1.56 | 3.73 | 5.17 |

Example 2

In Vivo Measurements

A clinical CT device (Siemens Volume Zoom, from Siemens Healthcare, Erlangen, Germany) was equipped with an additional filter of 0.25 mm Pb. This filter had been made of a Pb metal film (from Goodfellow GmbH, Bad Neuheim, Germany) and was fastened between two thin plastics carriers in the collimator housing of the CT device. The beam path was completely covered so that only filtered radiation was emitted. The CT device could thus be used for imaging without restriction. A narcotized rat was used for imaging. As the contrast medium substance, a tungsten-containing compound (W3O2-nona-acetate), as disclosed in the specification WO 97/03994, was used. This was administered intravenously via the tail vein by way of an infusion pump at a flow rate of 0.8 ml/s. The contrast medium dose was 300 mgW/kg body weight. At the same time as the contrast medium application, a dynamic CT measurement over a 20 s period was started, by way of which the contrast medium bolus was recorded over time at thorax height. For this purpose, every 0.8 s, a CT image was reconstructed at the identical slice position. This measurement was carried out with and without a Pb additional filter. The temporal interval between the measurements was 24 h in order to ensure complete elimination of the substance. The CT tube voltage was 120 kV at an mAs product of 625 mAs (with 0.25 mm Pb) and 231 mAs (without any additional filter). The mAs settings were selected based on the preceding phantom experiments, as described in example 1. Measurement of the radiation dose was carried out with an ionizing chamber (PTW 31010, from PTW, Freiburg, Germany) directly adjacent to the animal. On use of the lead additional filter, a dose of 93.7 mGy was measured and, without filter, of 130.2 mGy. For subsequent data processing, the time-signal curve in the aorta and in the muscles was determined. Table B5 shows the HU values during the peak of the contrast medium bolus in the aorta and the muscle. The standard deviation of the homogeneous tissue signals served to determine the noise level. The CNR as determined between the aorta and the surrounding muscle tissue, on use of the additional filter, was slightly higher than without the filter although only 72% of the radiation dose was used for image generation. This result is in good agreement with the in-vitro measurement (example 1), wherein at a radiation dose of 66%, an identical CNR can be generated (120 kV, 0.25 mm Pb filter).

TABLE B5

Quantitative evaluation of the CT measurements with (0.25 mm Pb) and without (0 mm Pb) additional filter: signal in the aorta (S1), noise in the aorta (R1), signal in the muscle (S2), noise in the muscle (R2), calculated contrast-to-noise ratio (CNR) and measured radiation dose (dose).

| Pb filter | S1 [HU] | R1 [HU] | S2 [HU] | R2 [HU] | CNR | Dose [mGy] |
|---|---|---|---|---|---|---|
| 0 mm | 745 | 16.9 | 56.1 | 9.0 | 36.3 | 130.2 |
| 0.25 mm | 889 | 19.2 | 53.6 | 8.7 | 40.1 | 93.7 |

Overall, therefore, the invention relates to a method for generating at least one X-ray image of a patient with incorporated contrast medium, using X-ray radiation with an energy spectrum and an X-ray detector, wherein the energy spectrum used is modified by at least one first filter arranged in the beam path in front of the patient, the patient absorbs a dose in order to generate detector data for the X-ray image and the X-ray image has a CNR value which represents the ratio of the maximum contrast in the image to the noise, wherein according to the invention, taking account of the thickness of the patient to be X-rayed, the energy spectrum and the contrast medium are adjusted to one another by an additional filter such that an optimization criterion taken from an experimentally generated or simulated X-ray image, is maximized.

Furthermore, an X-ray system for generating at least one X-ray image of a patient with incorporated contrast medium, by carrying out the method described, and the use of an embodiment of the inventive X-ray system in a variety of examinations are also proposed.

Although the invention has been illustrated and described in detail based on the preferred example embodiment, the invention is not restricted by the examples given and other variations can be derived therefrom by a person skilled in the art without departing from the protective scope of the invention.

What is claimed is:

1. A method for generating at least one X-ray image of a patient with incorporated contrast medium, the at least one X-ray image being generated using an X-ray detector and X-ray radiation generated at an anode, the X-ray radiation including an energy spectrum of braking rays and characteristic radiation, the method comprising:

modifying the energy spectrum by using at least one first filter arranged in a beam path in front of the patient, the at least one first filter being a beam hardening filter;

generating detector data for the X-ray image upon the patient absorbing a dose of X-ray radiation, the X-ray image including a contrast-to-noise ratio (CNR) value representing a ratio of a maximum contrast in the X-ray image to noise;

selecting an additional filter, from among a plurality of additional filters, to be inserted into the beam path in front of the patient to further adjust the energy spectrum, the additional filter being selected based on an examination protocol of the patient, the incorporated contrast medium, a tube voltage, and patient data, and the additional filter being selected according to a product of (i) a ratio ($CNR^2/D_y$) of the square of the contrast-to-noise ratio ($CNR^2$) of the X-ray image of the patient to the radiation dose ($D_y$) received by the patient for the X-ray image and (ii) a ratio ($CNR/D_K$) of the contrast-to-noise ratio (CNR) of the X-ray image of the patient to the contrast medium dose ($D_K$) incorporated into the patient;

moving the selected additional filter into the beam path in front of the patient to further adjust the energy spectrum, the energy spectrum being further adjusted taking into account a thickness of the patient; and generating the X-ray image of the patient with the incorporated contrast medium using the X-ray detector and X-ray radiation generated at the anode, the X-ray radiation including the energy spectrum of braking rays and characteristic radiation;

wherein the additional filter is composed of a filter material including at least one of iridium (atomic number Z=77), platinum (Z=78), gold (Z=79), mercury (Z=80), lead (Z=82), and bismuth (Z=83); and wherein a contrast-creating material in the contrast medium includes different materials or material combinations including at least one of rhenium (atomic number Z=75), hafnium (Z=72), tantalum (Z=73), tungsten (Z=74), and elements from the group of lanthanides (atomic number Z=58 to 71).

2. The method of claim 1, wherein a combination of absorbent material of the additional filter and the contrast-creating material of the contrast medium is selected such that the K-edge of the absorbent material of the additional filter lies energetically above the contrast-creating material of the contrast medium.

3. The method of claim 1, further comprising:
at least one of proposing and automatically adjusting, using a logic circuit or logic programming, at least one further variable recording parameter following determination or input of unchanging recording parameters.

4. The method of claim 3, wherein at least one of patient diameter, the contrast medium dose, material or element of the contrast medium, the CNR, and radiation dose to be applied are used as the unchanging recording parameters.

5. The method of claim 3, wherein at least one of maximum photon energy, anode material, the filter material of the additional filter, thickness of the additional filter, material or element of the contrast medium, the contrast medium dose, the CNR, and radiation dose to be applied, is used as a changeable recording parameter provided said parameter has not been selected as an unchanging recording parameter.

6. The method of claim 1, further comprising:
determining a mean thickness of the patient in a region to be recorded;

introducing test results from recordings with a plurality of different energy spectra, taking into account the mean thickness of the patient and determining associated CNR values between contrast medium-free tissue and contrast medium-enriched body fluid or tissue or between maximum and minimum image values from the overall image of the patient;

selecting a configuration of energy spectrum and contrast medium with a maximum value for the optimization criterion;

setting the selected configuration; and generating at least one projection of the patient using the selected configuration.

7. The method of claim 6, wherein
in taking into account the mean thickness of the patient in the recording region, only configurations of the maximum energy of the energy spectrum, additional filter material and contrast medium used are tested;

K-edges of the additional filter material lie between the maximum of the energy spectrum of the braking rays without additional filters and the maximum energy of the energy spectrum; and K-edges of the contrast medium lie between the maximum of the energy spectrum of the braking rays without additional filters and the K-edges of the additional filter material.

8. The method of claim 6, further comprising:
varying the maximum energy of the energy spectrum to vary the energy spectrum for the test results.

9. The method of claim 6, further comprising:
varying the anode material to vary the energy spectrum for the test results.

10. The method of claim 6, further comprising:
varying the layer thickness of at least one additional filter arranged in the beam path in front of the patient to vary the energy spectrum for the test results.

11. The method of claim 1, wherein the X-ray image of the patient is a projectional X-ray image.

12. The method of claim 1, wherein the X-ray image of the patient is a two-dimensional or three-dimensional tomographic image.

13. The method of claim 6, wherein the mean thickness of the patient in the recording region is determined by creating at least one topogram, at least in the recording region from at least one projection direction.

14. The method of claim 6, wherein the mean thickness of the patient in the recording region is determined by optical scanning at least in the recording region.

15. The method of claim 6, wherein the mean thickness of the patient in the recording region is estimated based on at least one of weight, height and sex data.

16. A method for making X-ray recordings in a combination of an X-ray system with contrast medium incorporated into a patient, wherein the contrast medium contains at least one of rhenium, hafnium, tantalum, and tungsten, and wherein a contrast-to-noise ratio between contrast medium-accumulating tissues and surrounding tissue is increased, the method comprising:

selecting at least one additional filter, from among a plurality of additional filters, to be inserted into a beam path in front of an X-ray tube to spectrally modify radiation emitted by the X-ray tube of the X-ray system, the at least one additional filter being selected based on an examination protocol of the patient, the incorporated contrast medium, a tube voltage, and patient data, and the at least one additional filter being selected according to a product of (i) a ratio ($CNR^2/D_y$)

of the square of the contrast-to-noise ratio ($CNR^2$) of an X-ray image of the patient to the radiation dose ($D_\gamma$) received by the patient for the X-ray image and (ii) a ratio ($CNR/D_K$) of the contrast-to-noise ratio (CNR) of the X-ray image of the patient to the contrast medium dose ($D_K$) incorporated into the patient; and moving the selected at least one additional filter into the beam path in front of the X-ray tube, the at least one additional filter being composed of a filter material including at least one element from a group of elements having the atomic numbers 77 (iridium), 78 (platinum), 79 (gold), 80 (mercury), 82 (lead), and 83 (bismuth).

17. A method for making X-ray recordings in an X-ray system with contrast media incorporated into a patient, wherein the contrast media contains at least one of rhenium, hafnium, tantalum, and tungsten, the method comprising:

selecting at least one additional filter, from among a plurality of additional filters, to be inserted into a beam path in front of an X-ray tube to spectrally modify radiation emitted by the X-ray tube of the X-ray system, the additional filter being selected based on an examination protocol of the patient, the incorporated contrast media, a tube voltage, and patient data, and the additional filter being selected according to a product of (i) a ratio ($CNR^2/D_\gamma$) of the square of the contrast-to-noise ratio ($CNR^2$) of an X-ray image of the patient to the radiation dose ($D_\gamma$) received by the patient for the X-ray image, and (ii) a ratio ($CNR/D_K$) of the contrast-to-noise ratio (CNR) of the X-ray image of the patient to the contrast medium dose ($D_K$) incorporated into the patient;

moving the selected at least one additional filter into the beam path, the at least one additional filter being composed of a filter material including at least one element from a group including elements with atomic numbers 77 (iridium), 78 (platinum), 79 (gold), 80 (mercury), 82 (lead), and 83 (bismuth);

reconstructing computer-assisted tomographic images using the spectrally modified radiation; and using the increase in image contrast, alongside the rise in image quality, to reduce at least one of the radiation and the contrast medium dose received by the patient.

18. The method of claim 16, wherein said method is used in CT angiography, dynamic contrast medium-assisted CT or contrast medium-assisted CT tumor diagnosis.

19. An X-ray system for generating at least one X-ray image of a patient with incorporated contrast medium, the X-ray system comprising:

at least one anode configured to generate X-ray radiation with an energy spectrum of braking rays and characteristic radiation;

at least one X-ray detector for pixel-wise measurement of the X-ray radiation penetrating the patient;

at least one filter arranged in a beam path between the at least one anode and the at least one X-ray detector in front of the patient, the at least one filter being configured to modify the energy spectrum, the at least one first filter being a beam hardening filter;

at least one computer processor configured to control the X-ray system during operation, generate detector data, and generate X-ray images based on the detector data; and at least one memory store in which computer programs with calculation and control instructions for execution by the at least one computer processor are stored, wherein at least one of the stored computer programs, when executed, causes the at least one computer processor to generate the detector data for an X-ray image upon the patient absorbing a dose of X-ray radiation, the X-ray image having a CNR value representing a ratio of a maximum contrast in the image to noise, select an additional filter, from among a plurality of additional filters, to be inserted into the beam path in front of the patient to further adjust the energy spectrum, the additional filter being selected based on an examination protocol of the patient, the incorporated contrast medium, a tube voltage, and patient data, and the additional filter being selected according to a product of (i) a ratio ($CNR^2/D_\gamma$) of the square of the contrast-to-noise ratio ($CNR^2$) of the X-ray image of the patient to the radiation dose ($D_\gamma$) received by the patient for the X-ray image, and (ii) a ratio ($CNR/D_K$) of the contrast-to-noise ratio (CNR) of the X-ray image of the patient to the contrast medium dose ($D_K$) incorporated into the patient, move the selected additional filter into the beam path in front of the patient to further adjust the energy spectrum, the energy spectrum being further adjusted taking account a thickness of the patient being X-rayed; and generate the X-ray image of the patient with the incorporated contrast medium using the X-ray detector and the X-ray radiation generated at the anode, the X-ray radiation including the energy spectrum of braking rays and characteristic radiation;

wherein the additional filter is composed of a filter material including at least one of iridium (atomic number Z=77), platinum (Z=78), gold (Z=79), mercury (Z=80), lead (Z=82), and bismuth (Z=83); and wherein a contrast-creating material in the contrast medium includes different materials or material combinations including at least one of rhenium (atomic number Z=75), hafnium (Z=72), tantalum (Z=73), tungsten (Z=74), and elements from the group of lanthanides (atomic number Z=58 to 71).

20. The X-ray system of claim 19, wherein said system is a C-arm system.

21. The X-ray system of claim 19, wherein said system is a computed tomography system.

22. The X-ray system of claim 19, wherein said system is a system exclusively for generating projectional X-ray images.

23. A method, comprising:
using the X-ray system of claim 19 in CT angiography to reduce the radiation dose received by the patient.

24. A method, comprising:
using the X-ray system of claim 19 in CT angiography to enhance the image quality and therefore the diagnostic validity, above all in coronary angiography and in the angiography of small and peripheral vessels.

25. A method, comprising:
using the X-ray system of claim 19 in dynamic contrast medium-assisted CT imaging such as multi-phase liver diagnostics, brain perfusion, tumor perfusion or myocardial perfusion in order to reduce the radiation dose received by the patient.

26. A method, comprising:
using the X-ray system of claim 19 in dynamic contrast medium-assisted CT imaging such as multi-phase liver diagnostics, brain perfusion, tumor perfusion or myocardial perfusion in order to enhance the image quality and thus the accuracy of functional parameters derived therefrom.

27. A method, comprising:
using the X-ray system of claim 19 in contrast medium-assisted CT tumor diagnostics to reduce the radiation dose received by the patient.

28. A method, comprising:
using the X-ray system of claim 19 in contrast medium-assisted CT tumor diagnostics to enhance image quality and also the diagnostic validity.

29. A method, comprising:
using the X-ray system of claim 19 in contrast medium-assisted CT imaging to reduce the contrast medium dose, above all for renal insufficiency patients or patients with contrast medium intolerance.

30. A method, comprising:
using the X-ray system of claim 19 in a dual energy CT examination of a patient, wherein the patient has one or more contrast media with different atomic numbers simultaneously or sequentially.

31. The method of claim 17, wherein said method is used in CT angiography, dynamic contrast medium-assisted CT or contrast medium-assisted CT tumor diagnosis.

* * * * *